(12) United States Patent
Appel et al.

(10) Patent No.: US 9,028,870 B2
(45) Date of Patent: *May 12, 2015

(54) HYDROGEL-DRIVEN DRUG DOSAGE FORM

(75) Inventors: Leah E. Appel, Bend, OR (US); Ronald A. Beyerinck, Bend, OR (US); Mark B. Chidlaw, Bend, OR (US); William J. Curatolo, Niantic, CT (US); Dwayne T. Friesen, Bend, OR (US); Kelly L. Smith, Bend, OR (US); Avinash G. Thombre, East Lyme, CT (US)

(73) Assignee: Bend Research, Inc., Bend, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/979,278

(22) Filed: Dec. 27, 2010

(65) Prior Publication Data

US 2011/0182947 A1 Jul. 28, 2011

Related U.S. Application Data

(60) Division of application No. 11/610,603, filed on Dec. 14, 2006, now abandoned, which is a continuation of application No. 09/745,095, filed on Dec. 20, 2000, now abandoned.

(60) Provisional application No. 60/171,968, filed on Dec. 23, 1999.

(51) Int. Cl.
*A61K 9/00* (2006.01)

(52) U.S. Cl.
CPC .................................. *A61K 9/0004* (2013.01)

(58) Field of Classification Search
CPC ..................................................... A61K 9/0004
See application file for complete search history.

(56) References Cited

U.S. PATENT DOCUMENTS

| | | | | |
|---|---|---|---|---|
| 4,795,641 A | * | 1/1989 | Kashdan | 424/438 |
| 5,001,147 A | * | 3/1991 | Baccichetti et al. | 514/454 |
| 5,096,716 A | * | 3/1992 | Deters et al. | 424/473 |
| 5,582,591 A | * | 12/1996 | Cheikh | 604/500 |

* cited by examiner

*Primary Examiner* — Trevor Love
(74) *Attorney, Agent, or Firm* — Klarquist Sparkman, LLP

(57) ABSTRACT

A controlled release dosage form has a coated core with the core comprising a drug-containing composition and a water-swellable composition, each occupying separate regions within the core. The drug-containing composition comprises a low-solubility drug and a drug-entraining agent. The coating around the core is water-permeable, water-insoluble and has at least one delivery port therethrough. A variety of formulations having specific drug release profiles are disclosed.

3 Claims, 1 Drawing Sheet

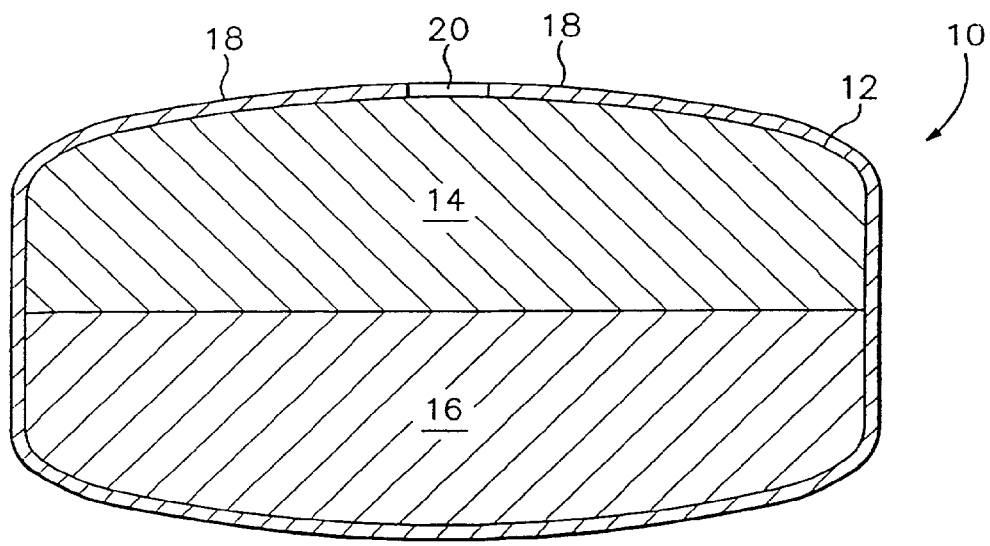

HYDROGEL-DRIVEN DRUG DOSAGE FORM

This is a divisional of U.S. application Ser. No. 11/610,603 filed Dec. 14, 2006, now abandoned which is a continuation of U.S. application Ser. No. 09/745,095 filed Dec. 20, 2000, now abandoned and claims priority of U.S. Application No. 60/171,968 filed Dec. 23, 1999.

BACKGROUND OF THE INVENTION

The present invention relates to a dosage form that provides a controlled release of a low-solubility beneficial agent, or drug, to an environment of use.

Osmotic and hydrogel-driven drug delivery devices for the release of a drug have been known in the art for some time. Exemplary dosage forms have included a tablet comprising a semipermeable wall surrounding a compartment containing the drug and a layer of swellable hydrogel, with the drug being delivered through a passageway in the semipermeable wall by swelling of the hydrogel, as described in U.S. Pat. No. 4,327,725; another tablet comprising a wall permeable to an exterior fluid but impermeable to the drug, the wall surrounding a compartment containing two osmotic agents, two expandable polymers and the drug, as described in U.S. Pat. No. 4,612,008; drug dispersed in a swellable hydrogel matrix core that releases the drug by diffusion into the environment of use, as described in U.S. Pat. No. 4,624,848; a hydrogel reservoir containing a multiplicity of tiny pills wherein each tiny pill consists of a wall surrounding a drug core, as described in U.S. Pat. No. 4,851,232; and a two-layered tablet wherein one layer is drug mixed with a hydrogel and the other layer is a hydrogel, as described in U.S. Pat. No. 5,516,527.

While the conventional dosage forms described above are functional, nonetheless such dosage forms suffer from a variety of drawbacks. A controlled release dosage form should ideally deliver substantially all of the drug from the dosage form to the environment of use. However, a common problem encountered by osmotic and hydrogel-driven dosage forms, particularly when the drug has low aqueous solubility, is that residual drug is left in the tablet interior after the hydrogel or other swellable material has completely swelled. This residual drug is not available for absorption and, accordingly, such dosage forms require increased amounts of drug to compensate for the failure of the system to release all of the drug into the environment of use.

In addition, the controlled release dosage form must operate within certain size constraints, and yet be capable of delivering most or all of the drug to the environment of use. Dosage forms, particularly for humans, are limited in size, and are usually less than 1 gram, more preferably less than 700 mg in weight. However, for some types of drugs, the dose amount may make up to half or even more of the weight of the dosage form. The water-swellable materials that provide the delivery of the drug must in instances where the dose is high be capable of providing a highly efficient delivery of the drug, since very little of the dosage form may be available for the swellable material or other excipients.

In addition, it is often desired that the dosage form begin extruding drug relatively quickly upon entering the use environment. However, many delivery systems exhibit a time lag before extruding drug. This is particularly a problem when the drug has low aqueous solubility or is hydrophobic. Several techniques have been proposed to reduce the time lag, but each has its own drawback. One technique has been to provide high-permeability coatings by utilizing thin coatings around the dosage form. While this technique provides a quicker uptake of fluid, the thin coating lacks strength and often bursts in use or provides insufficient protection to the dosage form which becomes susceptible to damage during handling. Yet another technique has involved providing pores or one or more passageways that communicate with the water-swellable materials, but this often leads to unacceptable amounts of residual drug. Another technique involves coating the dosage form with an immediate release drug formulation, but this requires additional processing steps and provides a dosage form with two different release rates, which may be undesirable.

Yet another problem encountered with conventional osmotic and hydrogel-driven drug delivery systems is that such dosage forms often require the presence of osmagents. Osmagents are selected such that they generate an osmotic pressure gradient across the barrier of the surrounding coating. The osmotic pressure gradient drives the permeation of water into the tablet and the resulting buildup of sufficient hydrostatic pressure, which forces the drug through the delivery port. These osmagents increase the weight of the dosage form, thus limiting the amount of drug which may be contained in the dosage form. In addition, the presence of additional ingredients in the dosage form, such as osmagents, increases the costs of manufacture due to the need to insure uniform concentrations of the ingredients throughout the dosage form, and may have other drawbacks such as adverse effects on compression properties and on drug stability.

Accordingly, there is still a need in the art for a controlled release dosage form that results in a highly efficient delivery of drug to an environment of use with very little residual drug, that allows large drug loading so as to minimize the dosage size, that begins releasing drug soon after entering the environment of use, and that limits the number of necessary ingredients. These needs and others which will become apparent to one skilled in the art are met by the present invention, which is summarized and described in detail below.

BRIEF SUMMARY OF THE INVENTION

The various aspects of the invention each provide a controlled release drug dosage form having a core comprising a drug-containing composition and a water-swellable composition. The drug-containing composition and the water-swellable composition occupy separate regions within the core. The drug-containing composition comprises a low-solubility drug and a drug-entraining agent. A coating around the core is water-permeable, water-insoluble and has at least one delivery port therethrough.

In a first aspect of the invention, the drug-containing composition further includes a swelling agent having a swelling ratio of at least 3.5, and the drug-entraining agent comprises at least 15 wt % of the drug-containing composition.

In a second aspect of the invention, the mass ratio of the drug-containing composition to the water-swellable composition has a value of at least 1.5, and the water-swellable composition comprises a water-swellable agent and a tableting aid, the water-swellable composition having a swelling ratio of at least 3.5, and a strength of at least 3 Kp/cm$^2$ (where Kp is Kiloponds).

In a third aspect of the invention, the water-swellable composition comprises a swelling agent. The coating around the core has a minimum durability of 1 Kp/cm$^2$, and a minimum water flux (40/75) of at least $1.0 \times 10^{-3}$ gm/cm$^2$-hr.

In a fourth aspect of the invention, the coating is porous and is formed from a substantially homogeneous solution comprising a solvent, a hydrophilic cellulosic polymer, and a non-solvent.

In a fifth aspect of the invention, the drug-containing composition further comprises a fluidizing agent. Following introduction into an environment of use, the dosage form releases at least about 70 wt % of the low-solubility drug to the use environment within about 12 hours.

In a sixth aspect of the invention, the drug-containing composition further comprises a solubilizer. When the drug is a basic drug, the solubilizer may be an organic acid.

In a seventh aspect of the invention, the low-solubility drug is in the form of an amorphous dispersion.

In an eighth aspect of the invention, a method is provided for treating a patient in need of a drug by administering a therapeutically effective amount of the drug in a dosage form of the invention.

In one embodiment, the dosage form includes a concentration-enhancing polymer.

The various aspects of the present invention have one or more of the following advantages. The dosage forms of the present invention are capable of delivering greater amounts of drug to the desired environment of use with greater efficiency using smaller amounts of swelling materials, and also result in lower amounts of residual drug than do conventional compositions. The compositions are also capable of higher drug loading compared with conventional compositions. In addition, the compositions begin delivering drug to the environment of use more quickly than do conventional osmotic controlled release dosage forms. The dosage forms are capable of rapidly delivering a low-solubility drug without the coating failing due to rupture as a result of excessive pressure within the core when the dosage form is introduced into an environment of use. The dosage forms are also capable of delivering a low-solubility drug in a solubilized form.

The foregoing and other objectives, features, and advantages of the invention will be more readily understood upon consideration of the following detailed description of the invention, taken in conjunction with the accompanying drawing.

BRIEF DESCRIPTION OF THE DRAWING

FIG. 1 is a schematic drawing of a cross section of an exemplary embodiment of a dosage form of the present invention.

DETAILED DESCRIPTION OF THE INVENTION

The present invention provides a controlled release dosage form that is specifically designed to provide controlled release of a low-solubility drug primarily by imbibition of water and extrusion of drug from the dosage form as opposed to primarily by diffusion. FIG. 1 shows an exemplary dosage form 10 having a core 12 comprising a drug-containing composition 14 and a water-swellable composition 16. The drug-containing composition and the water-swellable composition occupy separate regions in the core. By "separate regions" is meant that the two compositions occupy separate volumes, such that the two are not substantially mixed together. Of course, a small amount of intermixing of the compositions may occur where the compositions come in contact with each other, for example, at the interface between two layers. A coating 18 surrounds the core 12 and is water-permeable, water-insoluble and has one or more delivery ports 20 therethrough. In use, the core 12 imbibes water through the coating 18 from the environment of use such as the gastrointestinal ("GI") tract. The imbibed water causes the water-swellable composition 16 to swell, thereby increasing the pressure within the core 12. The imbibed water also increases the fluidity of the drug-containing composition. The pressure difference between the core 12 and the environment of use drives the release of the fluidized drug-containing composition 14. Because the coating 18 remains intact, the drug-containing composition 14 is extruded out of the core 12 through the delivery port(s) 20 into the environment of use. Because the water-swellable composition 16 contains no drug, almost all of the drug is extruded through the delivery port(s) 20, leaving very little residual drug.

The dosage form of the present invention releases the drug to an environment of use primarily by "extrusion" rather than by diffusion. The term "extrusion" as used herein is intended to convey an expulsion or forcing out of some or all of the drug through one or more delivery ports or pores in the coating to the exterior of the dosage form by hydrostatic forces, to be distinguished from delivery by a diffusion mechanism or by erosion of the mass of the device. The drug may be released primarily by extrusion either in the form of a suspension of solids in aqueous solution or the drug may be in solution, to the extent dissolution has taken place in the core 12.

Reference to the "release" of drug as used herein means (1) transport of drug from the interior of the dosage form to its exterior such that it contacts the fluid within a mammal's GI tract following delivery or (2) transport of drug from the interior of the dosage form such that it contacts a test medium for evaluation of the dosage form by an in vitro test as described below. Reference to a "use environment" can thus be either to in vivo GI fluids or to an in vitro test medium. "Introduction" to a use environment includes either by ingestion or swallowing or use of implants or suppositories, where the use environment is in vivo, or being placed in a test medium where the use environment is in vitro.

Release Characteristics

An important attribute of the dosage forms of the present invention is the delivery of drug to a use environment in a controlled manner. The dosage forms provide drug concentration release profiles that meet the following criteria.

First, in some aspects of the present invention, the dosage forms start releasing drug soon after introduction to the use environment. When a rapid onset of delivery is desired, preferably the dosage forms release at least 5 wt % of the drug, and more preferably at least 10 wt % of the drug within 2 hours after introduction to the use environment, where these percentages correspond to the mass of drug released from the core relative to the total mass of drug originally present in the core. By quickly beginning the release of the drug, the dosage form shortens the time required to achieve a maximum drug concentration in a use environment and increases the total amount of time during which the drug is in a use environment, resulting in increased absorption and greater bioavailability.

Second, the dosage forms release the drug in a controlled manner, preferably at a substantially constant rate. Thus, the dosage forms release no more than about 60 wt % of the drug, and preferably no more than about 50 wt % of the drug, into the use environment within 2 hours after introduction to the use environment.

Third, the rate of release of drug from the dosage form should be sufficiently high to allow release of the drug within a time frame that allows a substantial fraction of the drug delivered to be absorbed into the blood stream. Specifically, the dosage forms release at least 60 wt % of the drug, and preferably at least 70 wt % of the drug to the use environment within 16 hours after introduction to the use environment. The inclusion of a fluidizing agent in the drug-containing composition is particularly useful when more rapid delivery of drug to the use environment is desired. In particular, when it is desirable to deliver at least 70 wt % of the drug to the use environment within 12 hours after introduction thereto, the invention allows rapid drug release without rupture or otherwise failure of the dosage form coating during operation.

Fourth, the dosage forms release a substantial amount of the drug contained within the dosage form, leaving a relatively small residual amount of drug after 24 hours. Obtaining low residual amounts of drug is particularly difficult when it is desired to deliver high doses of low-solubility drug. The dosage forms of the present invention release at least 80 wt % of drug, preferably at least 90 wt %, and more preferably at least 95 wt % of drug to the use environment within 24 hours after introduction of the dosage form to the use environment.

An in vitro test may be used to determine whether a dosage form provides a release profile within the scope of the present invention. In vitro tests are well known in the art. An example is a "residual test," which is described below for sertraline HCl. The dosage form is first placed into a stirred USP type 2 dissoette flask containing 900 mL of a buffer solution simulating gastric environment (10 mM HCl, 100 mM NaCl, pH 2.0, 261 mOsm/kg) at 37° for 2 hours, then removed, rinsed with deionized water, and transferred to a stirred USP type 2 dissoette flask containing 900 mL of a buffer solution simulating the contents of the small intestine (6 mM $KH_2PO_4$, 64 mM KCl, 35 mM NaCl, pH 7.2, 210 mOsm/kg). In both flasks, the dosage form is placed in a wire support to keep the dosage form off of the bottom of the flask, so that all surfaces are exposed to the moving release solution and the solutions are stirred using paddles that rotate at a rate of 50 rpm. At each time interval, a single dosage form is removed from the solution, released material is removed from the surface, and the dosage form cut in half and placed in 100 mL of a recovery solution (1:1 wt/wt ethanol:water, pH adjusted to 3 with 0.1 N HCl), and vigorously stirred overnight at ambient temperature to dissolve the drug remaining in the dosage form. Samples of the recovery solution containing the dissolved drug are filtered using a Gelman Nylon® Acrodisc® 13, 0.45 μm pore size filter, and placed in a vial and capped. Residual drug is analyzed by HPLC. Drug concentration is calculated by comparing UV absorbance of samples to the absorbance of drug standards. The amount remaining in the tablets is subtracted from the total drug to obtain the amount released at each time interval.

An alternative in vitro test is a direct test, in which samples of the dosage form are placed into a stirred USP type 2 dissoette flask containing 900 mL of a receptor solution such as USP sodium acetate buffer (27 mM acetic acid and 36 mM sodium acetate, pH 4.5) or 88 mM NaCl. Samples are taken at periodic intervals using a VanKel VK8000 autosampling dissoette with automatic receptor solution replacement. Tablets are placed in a wire support as above, paddle height is adjusted, and the dissoette flasks stirred at 50 rpm at 37° C. The autosampler dissoette device is programmed to periodically remove a sample of the receptor solution, and the drug concentration is analyzed by HPLC using the procedure outlined above. Since the drug is usually extruded from the dosage form as a suspension in an entraining polymer, there is often a time lag between when the drug is released and when it is dissolved in the test medium, and thus, measured in the direct test. This time lag depends on the solubility of the drug, the test medium, and the ingredients of the drug-containing composition, but typically is on the order of 30 to 90 minutes.

Alternatively, an in vivo test may be used to determine whether a dosage form provides a drug release profile within the scope of the present invention. However, due to the inherent difficulties and complexity of the in vivo procedure, it is preferred that in vitro procedures be used to evaluate dosage forms even though the ultimate use environment is often the human GI tract. Drug dosage forms are dosed to a group of humans or dogs and drug release and drug absorption is monitored either by (1) periodically withdrawing blood and measuring the serum or plasma concentration of drug or (2) measuring the amount of drug remaining in the dosage form following its exit from the anus (residual drug) or (3) both (1) and (2). In the second method, residual drug is measured by recovering the tablet upon exit from the anus of the test subject and measuring the amount of drug remaining in the dosage form using the same procedure described above for the in vitro residual test. The difference between the amount of drug in the original dosage form and the amount of residual drug is a measure of the amount of drug released during the mouth-to-anus transit time. This test has limited utility since it provides only a single drug release time point but is useful in demonstrating the correlation between in vitro and in vivo release.

In one in vivo method of monitoring drug release and absorption, the serum or plasma drug concentration is plotted along the ordinate (y-axis) against the blood sample time along the abscissa (x-axis). The data may then be analyzed to determine drug release rates using any conventional analysis, such as the Wagner-Nelson or Loo-Riegelman analysis. See also Welling, "Pharmacokinetics: Processes and Mathematics" (ACS Monograph 185, *Amer. Chem. Soc.*, Washington, D.C., 1986). Treatment of the data in this manner yields an apparent in vivo drug release profile.

Drug-Containing Composition

Referring again to FIG. 1, The drug-containing composition 14 of the core 12 of the dosage form 10 includes at least a low-solubility drug and an entraining agent, and preferably additional excipients. The drug-containing composition occupies a separate, substantially distinct region from the water-swellable composition, and comprises about 50 to 90 wt % of the core, preferably 60 to 85 wt % of the core, and more preferably greater than 70 wt % of the core. Preferably, the drug-containing composition 14 is in contact with the coating 18 which surrounds the dosage form.

The drug may be virtually any beneficial therapeutic agent and may comprise from 0.1 to 65 wt % of the drug-containing composition 14. In cases where the dose to be delivered is high, it is preferred that the drug comprise at least 35 wt % of the drug-containing composition 14. The drug may be in any form, either crystalline or amorphous. The drug may also be in the form of a solid dispersion. The invention finds particular utility when the drug is a "low-solubility drug." In this context, "low-solubility drug" generally means that the solubility is sufficiently low that, during operation within a use environment, at least a portion of the drug remains undissolved and therefore is delivered as a suspension. In the small volume of a coated tablet, the drug solubility and dose-to-aqueous solubility ratio must be quite high in order for all of the drug to dissolve and be delivered as a solution. Specifically, by "low-solubility drug" we mean that the drug is either "substantially water-insoluble" (which means that the drug has a minimum aqueous solubility at physiologically relevant pH (e.g., pH 1-8) of less than 0.01 mg/mL), or "sparingly water soluble," that is, has a minimum aqueous solubility at physiologically relevant pH up to about 1 to 2 mg/mL, or has even low to moderate aqueous solubility, having a minimum aqueous solubility at physiologically relevant pH as high as about 20 to 40 mg/mL. In general, it may be said that the drug has a dose-to-aqueous solubility ratio greater than 10 mL, and more typically greater than 100 mL, where the drug solubility is the minimum value in mg/mL observed in any physiologically relevant aqueous solution (e.g., those with pH values between 1 and 8) including USP simulated gastric and intestinal buffers and the dose is in mg. The drug may be employed in its neutral (e.g., free acid, free base or zwitterion) form, or in the form of its pharmaceutically acceptable salts as well as in anhydrous, hydrated, or solvated forms, and pro drugs.

Preferred classes of drugs include, but are not limited to, antihypertensives, antidepressants, antianxiety agents, anticlotting agents, anticonvulsants, blood glucose-lowering agents, decongestants, antihistamines, antitussives, anti-inflammatories, antipsychotic agents, cognitive enhancers, cholesterol-reducing agents, cholesterol ester transfer protein inhibitors, high-density lipoprotein enhancers, antiobesity agents, autoimmune disorders agents, anti-impotence agents, antibacterial and antifungal agents, hypnotic agents, anti-Parkinsonism agents, antibiotics, antiviral agents, anti-neoplastics, barbituates, sedatives, nutritional agents, beta blockers, emetics, anti-emetics, diuretics, anticoagulants, cardiotonics, androgens, corticoids, anabolic agents, growth hormone secretagogues, anti-infective agents, coronary vasodilators, carbonic anhydrase inhibitors, antiprotozoals, gastrointestinal agents, serotonin antagonists, anesthetics, hypoglycemic agents, dopaminergic agents, anti-Alzheimer's Disease agents, anti-ulcer agents, platelet inhibitors and glycogen phosphorylase inhibitors.

Specific examples of the above and other classes of drugs and therapeutic agents deliverable by the invention are set forth below, by way of example only. Specific examples of antihypertensives include prazosin, nifedipine, trimazosin, amlodipine, and doxazosin mesylate; a specific example of an antianxiety agent is hydroxyzine; a specific example of a blood glucose lowering agent is glipizide; a specific example of an anti-impotence agent is sildenafil citrate; specific examples of anti-neoplastics include chlorambucil, lomustine and echinomycin; specific examples of anti-inflammatory agents include betamethasone, prednisolone, piroxicam, aspirin, flurbiprofen and (+)-N-{4-[3-(4fluorophenoxy)phenoxy]-2-cyclopenten-1-yl}-N-hydroxyurea; a specific example of a barbituate is phenobarbital; specific examples of antivirals include acyclovir, nelfinavir, and virazole; specific examples of vitamins/nutritional agents include retinol and vitamin E; specific examples of a β-blocker include timolol and nadolol; a specific example of an emetic is apomorphine; specific examples of a diuretic include chlorthalidone and spironolactone; a specific example of an anticoagulant is dicumarol; specific examples of cardiotonic include digoxin and digitoxin; specific examples of an androgen include 17-methyltestosterone and testosterone; a specific example of a mineral corticoid is desoxycorticosterone; a specific example of a steroidal hypnotic/anesthetic is alfaxalone; specific examples of an anabolic agent include fluoxymesterone and methanstenolone; specific examples of antidepression agents include fluoxetine, pyroxidine, venlafaxine, sertraline, paroxetine, sulpiride, [3,6-dimethyl-2-(2, 4,6-trimethyl-phenoxy)-pyridin-4-yl]-(lethylpropyl)-amine and 3,5-dimethyl-4-(3'-pentoxy)-2-(2',4',6'-trimethylphenoxy)pyridine; specific examples of an antibiotic include ampicillin and penicillin G; specific examples of an anti-infective include benzalkonium chloride and chlorhexidine; specific examples of a coronary vasodilator include nitroglycerin and mioflazine; a specific example of a hypnotic is etomidate; specific examples of a carbonic anhydrase inhibitor include acetazolamide and chlorzolamide; specific examples of an antifungal include econazole, terconazole, fluconazole, voriconazole and griseofulvin; a specific example of an antiprotozoal is metronidazole; a specific example of an imidazole-type anti-neoplastic is tubulazole; specific examples of an anthelmintic agent include thiabendazole, oxfendazole and morantel; specific examples of an antihistaminic include astemizole, levocabastine, cetirizine, and cinnarizine; a specific example of a decongestant is pseudoephedrine; specific examples of antipsychotics include fluspirilene, penfluridole, risperidone and ziprasidone; specific examples of a gastrointestinal agent include loperamide and cisapride; specific examples of a serotonin antagonist include ketanserin and mianserin; a specific example of an anesthetic is lidocaine; a specific example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer agents are THA and donepezil; a specific example of an anti-ulcer agent/H2 antagonist is famotidine; specific examples of a sedative/hypnotic include chlordiazepoxide and triazolam; a specific example of a vasodilator is alprostadil; a specific example of a platelet inhibitor is prostacyclin; specific examples of an ACE inhibitor/antihypertensive include enalaprilic acid and lisinopril; specific examples of a tetracycline antibiotic include oxytetracycline and minocycline; specific examples of a macrolide antibiotic include azithromycin, clarithromycin, erythromycin and spiramycin; specific examples of glycogen phosphorylase inhibitors include [R—(R*S*)]-5-Chloro-N-[2-hydroxy-3-{methoxymethylamino}-3-oxo-1-(phenylmethyl)-propyl]-1H-indole-2-carboxamide and 5-chloro-1H-indole-2-carboxylic acid [(1S)-benzyl-(2R)-hydroxy-3((3R,4S)-dihydroxy-pyrrolidin-1-yl-)-oxypropyl]amide.

Further examples of drugs deliverable by the invention are the glucose-lowering drug chlorpropamide, the anti-fungal fluconazole, the anti-hypercholesterodemic atorvastatin, the antipsychotic thiothixene, the anxiolytics hydroxyzine and doxepin, the anti-hypertensive amlodipine, the antiinflammatories piroxicam, celicoxib, valdicoxib and carprofen, and the antibiotics carbenicillin indanyl, bacampicillin, troleandomycin, and doxycycline.

In an alternative embodiment, the drug is present in the form of a solid, amorphous dispersion. By solid, amorphous dispersion is meant that the drug is dispersed in a polymer so that a major portion of the drug is in a substantially amorphous or non-crystalline state, and its non-crystalline nature is demonstrable by x-ray diffraction analysis or by differential scanning calorimetry. The dispersion may contain from about 5 to 90 wt % drug, preferably 10 to 70 wt %. The polymer is aqueous-soluble and inert, and is preferably concentration-enhancing. Suitable polymers and methods for making solid amorphous dispersions are disclosed in commonly assigned U.S. patent application Ser. Nos. 09/459,059 and 09/495,061, the relevant disclosures of which are incorporated by reference. Suitable dispersion polymers include ionizable and non-ionizable cellulosic polymers, such as cellulose esters, cellulose ethers, and cellulose esters/ethers; and vinyl polymers and copolymers having substituents selected from the group consisting of hydroxyl, alkylacyloxy, and cyclicamido, such as polyvinyl pyrrolidone, polyvinylalcohol, copolymers of polyvinyl pyrrolidone and polyvinyl acetate. Particularly preferred polymers include hydroxypropylmethyl cellulose acetate succinate (HPMCAS), hydroxypropyl methyl cellulose (HPMC), hydroxypropyl methyl cellulose phthalate (HPMCP), cellulose acetate phthalate (CAP), cellulose acetate trimellitate (CAT), and polyvinyl pyrrolidone (PVP). Most preferred are HPMCAS, HPMCP, CAP and CAT.

The drug-containing composition 14 must include an entraining agent. The use of an entraining agent is necessitated by the low-solubility drug, which due to its low-solubility does not dissolve sufficiently within the core 12 to be extruded in the absence of an entraining agent. The entraining agent suspends or entrains the drug so as to aid in the delivery of the drug through the delivery port(s) 20 to the environment of use. While not wishing to be bound by any particular theory, it is believed that upon imbibing water into the dosage form, the entraining agent imparts sufficient viscosity to the drug-containing composition to allow it to suspend or entrain the drug, while at the same time remaining sufficiently fluid to allow the entraining agent to pass through the delivery port(s) 20 along with the drug. It has been found that there is a good correlation between the usefulness of a material as an entraining agent and the viscosity of an aqueous solution of the material. The entraining agent generally is a material that has high water solubility and in operation forms aqueous solutions with viscosities of at least 50 centipoise (cp) and preferably aqueous solutions with viscosities of 200 cp or greater.

The amount of the entraining agent present in the drug-containing composition may range from about 20 wt % to about 98 wt % of the drug-containing composition. The entraining agent may be a single material or a mixture of materials. Examples of such materials include polyols, and oligomers of polyethers, such as ethylene glycol oligomers or propylene glycol oligomers. In addition, mixtures of polyfunctional organic acids and cationic materials such as amino acids or multivalent salts, such as calcium salts may be used. Of particular utility are polymers such as polyethylene oxide (PEO), polyvinyl alcohol, PVP, cellulosics such as hydroxyethyl cellulose (HEC), hydroxypropylcellulose (HPC), HPMC, methyl cellulose (MC), carboxy methyl cellulose (CMC), carboxyethylcellulose (CEC), gelatin, xanthan gum or any other water-soluble polymer that forms an aqueous solution with a viscosity similar to that of the polymers listed above. An especially preferred entraining agent is non-crosslinked PEO or mixtures of PEO with the other materials listed above.

When the low-solubility drug and a polymeric entraining agent make up about 80 wt % or more of the drug-containing composition, then the entraining agent, should have a sufficiently low molecular weight that it becomes sufficiently fluid so that both the drug and entraining agent can be rapidly extruded from the dosage form, instead of swelling and rupturing the water-permeable coating that surrounds the dosage form. Thus, for example, when PEO is the drug-entraining agent, it is generally preferred that it have a molecular weight of from about 100,000 to about 300,000 daltons. (References to molecular weights of polymers herein and in the claims are to average molecular weights.)

When the low-solubility drug and the entraining agent make up less than about 80 wt % of the drug-containing composition, a smaller portion of a more viscous entraining agent is preferred. For example, when the entraining agent is PEO, a lower fraction of a higher molecular weight of PEO from about 500,000 to 800,000 daltons may be used. Thus, there is an inverse relationship between the preferred PEO molecular weight and the weight fraction of the drug-containing composition that is drug and entraining agent. Thus, as the weight fraction decreases from about 0.9 to about 0.8, to about 0.7, to about 0.6, the preferred PEO molecular weight increases from about 200,000 daltons to about 400,000 daltons, to about 600,000 daltons, to about 800,000 daltons, respectively, and the weight fraction of entraining agent correspondingly decreases (the weight fraction of drug being relatively constant). It should be noted that for a particular formulation, the optimum PEO molecular weight for the entraining agent may vary higher or lower than those values by 20% to 50%. Likewise, when selecting an appropriate molecular weight of other polymeric entraining agents such as HEC, HPC, HPMC, or MC, as the weight fraction of entraining agent in the drug-containing composition is reduced, a higher molecular weight for the entraining agent is generally preferred.

In one embodiment of the invention, the drug-containing composition comprises a swelling agent in addition to the low-solubility drug and the drug-entraining agent. The swelling agent is generally a water-swellable polymer that substantially expands in the presence of water. Inclusion of even a small amount of such a swellable polymer can significantly enhance the onset, rate, and completeness of drug delivery. The degree of swelling of a swelling agent can be assessed by compressing particles of the swelling agent in a press to form a compact of the material having a "strength" ranging from 3 to 16 Kp/cm$^2$, where strength is the hardness of the compact in Kp as measured with a Schleuniger Tablet Hardness Tester, model 6D, divided by its maximum cross-sectional area normal to the direction of force in cm$^2$. For example, about 500 mg of a swelling agent can be compressed in a 13/32-inch die using an "f press." The swelling of a compact is measured by placing it between two porous glass frits in a glass cylinder and contacting it with a physiologically relevant test medium, such as simulated gastric or intestinal buffer, or water. The volume of the water-swollen compact after 16 to 24 hours contact with the test medium divided by its initial volume is termed the "swelling ratio" of the swelling agent. Generally, swelling agents suitable for inclusion in the drug layer are those water-swellable polymers that have swelling ratios, when water is the test medium, of at least 3.5, preferably greater than 5.

A preferred class of swelling agents comprises ionic polymers. Ionic polymers are generally polymers that have a significant number of functional groups that are substantially ionized in an aqueous solution over at least a portion of the physiologically relevant pH range 1 to 8. Such ionizable functional groups include carboxylic acids and their salts, sulfonic acids and their salts, amines and their salts, and pyridine salts. To be considered an ionic polymer, the polymer should have at least 0.5 milli-equivalents of ionizable functional groups per gram of polymer. Such ionic polymer swelling agents include sodium starch glycolate, sold under the trade name EXPLOTAB, and croscarmellose sodium, sold under the trade name AC-DI-SOL.

In one embodiment of the invention in which the drug-containing composition comprises a low-solubility drug, a drug-entraining agent, and a swelling agent, the swelling agent is present in an amount ranging from about 2 to about 20 wt % of the drug-containing composition 14. In other embodiments of the invention, the swelling agent is optionally present in an amount ranging from 0 to about 20 wt %.

In another embodiment of the present invention, the drug-containing composition further comprises a fluidizing agent. As used herein, a "fluidizing agent" is a water-soluble compound that allows the drug-containing composition to rapidly become fluid upon imbibing water when the dosage form is introduced into a use environment. Rapid fluidization of the drug-containing composition allows the composition to be extruded from the dosage form without a build-up of excessive pressure. This results in a relatively short time lag. That is, the time between introduction of the dosage form into the environment of use and the onset of drug delivery is relatively short. In addition, the inclusion of a fluidizing agent reduces the pressure within the core and thus reduces the risk of failure of the coating that surrounds the core of the dosage form. This is particularly important when a relatively rapid rate of drug release is desired, necessitating the use of a highly water-permeable coating that conventionally is relatively thin and weak. (By a rapid rate of release is generally meant that greater than 70 wt % of the low-solubility drug originally present in the dosage form is released within 12 hours of the time the dosage form is introduced into the use environment.)

The fluidizing agent can be essentially any water-soluble compound that rapidly increases the fluidity of the drug-containing composition when water is imbibed into the core. Such compounds generally have aqueous solubilities of at least 30 mg/mL and generally have a relatively low molecular weight (less than 10,000 daltons) such that upon imbibing a given quantity of water, the drug-containing composition rapidly becomes more fluid relative to a similar drug-containing composition that does not include the fluidizing agent. By more fluid is meant that the pressure required to extrude the drug through the delivery port(s) is lower than a similar composition without the fluidizing agent. This increased fluidity can be temporary, meaning that the increased fluidity occurs for only a short time after introduction of the dosage form to a use environment (e.g., 2 hours), or the increased fluidity can occur over the entire time the dosage form is in the use environment. Exemplary fluidizing agents are sugars, organic acids, amino acids, polyols, salts, and low-molecular weight oligomers of water-soluble polymers. Exemplary sugars are glucose, sucrose, xylitol, fructose, lactose, mannitol, sorbitol, maltitol, and the like. Exemplary organic acids are citric acid, lactic acid, ascorbic acid, tartaric acid, malic acid, fumaric, and succinic acid. Exemplary amino acids are alanine and glycine. Exemplary polyols are propylene glycol and sorbitol. Exemplary oligomers of low-molecular weight polymers are polyethylene glycols with molecular weights of 10,000 daltons or less. Particularly preferred fluidizing agents are sugars and organic acids. Such fluidizing agents are preferred as they often improve tableting and compression properties of the drug-containing composition relative to other fluidizing agents such as inorganic salts or low-molecular weight polymers.

In order for the fluidizing agent to rapidly increase the fluidity of the drug-containing composition at low water levels in the core 12 of the dosage form, the fluidizing agent must generally be present in an amount such that it makes up at least about 10 wt % of the drug-containing composition 14. To ensure that the drug-containing composition 14 does not become so fluid such that the drug-entraining agent cannot properly entrain or suspend the drug, particularly long after (12 hours or longer) introduction of the dosage form into the use environment, the amount of fluidizing agent generally should not exceed about 60 wt % of the drug-containing composition. In addition, as mentioned above, when a fluidizing agent is included, a drug-entraining agent with a higher molecular weight and correspondingly higher viscosity is generally included in the drug-containing composition, but at a lower level. Thus, for example, when the drug-containing composition comprises about 20 to 30 wt % of the low-solubility drug and about 30 wt % of a fluidizing agent such as a sugar, about 20 to 50 wt % of a high molecular weight polymer such as PEO with a molecular weight of about 500,000 to 800,000 daltons is preferable to a lower molecular weight PEO.

The drug-containing composition 14 may further include solubility-enhancing agents that promote the aqueous solubility of the drug, present in an amount ranging from about 0 to about 30 wt % of the drug-containing composition 14. Examples of suitable solubility-enhancing agents include surfactants; pH control agents such as buffers, organic acids and organic acid salts and organic and inorganic bases; glycerides; partial glycerides; glyceride derivatives; polyhydric alcohol esters; PEG and PPG esters; polyoxyethylene and polyoxypropylene ethers and their copolymers; sorbitan esters; polyoxyethylene sorbitan esters; carbonate salts; and cyclodextrins.

There are a variety of factors to consider when choosing an appropriate solubilizing agent for a drug. The solubilizing agent should not interact adversely with the drug. In addition, the solubilizing agent should be highly efficient, requiring minimal amounts to effect the improved solubility. It is also desired that the solubilizing agent have a high solubility in the use environment. For acidic, basic, and zwitterionic drugs, organic acids, organic acid salts, and organic and inorganic bases and base salts are known to be useful solubilizing agents. It is desired that these compounds have a high number of equivalents of acid or base per gram. The selection of solubilizing agent will therefore be highly dependent on the properties of the drug.

A preferred class of solubilizers for basic drugs is organic acids. Since basic drugs are solubilized by protonation, and since the solubility of basic drugs in an aqueous environment of pH 5 or higher is reduced and often may reach an extremely low value by pH 7.5 (as in the colon), it is believed that addition of an organic acid to the dosage form for delivery to the use environment with such drugs assists in solubilization and hence absorption of the drug. An exemplary basic drug is sertraline, which has moderate solubility at low pH, low solubility at pH values above 5 and extremely low solubility at pH of about 7.5. Another example of a basic drug that may benefit from an acidic solubilizer is ziprasidone. Even a slight decrease in the pH of the aqueous solution at high pH may result in dramatic increases in the solubility of basic drugs. In addition to simply lowering the pH, the presence of organic acids and their conjugate bases also raises the solubility at a given pH if the conjugate base salt of the basic drug has a higher solubility than the neutral form or the chloride salt of the drug.

It has been found that a preferred subset of organic acids meeting such criteria consists of citric, succinic, fumaric, adipic, malic and tartaric acids. The table below gives properties of these organic acids. Of these, fumaric and succinic are especially preferred when a high ratio of equivalents of acid per gram is desired. In addition, citric, malic, and tartaric acid have the advantage of extremely high water solubility. Succinic acid offers a combination of both moderate solubility and a high acid equivalent per gram value. Thus, the use of a highly soluble organic acid serves multiple purposes: it improves the solubility of the basic drug, particularly when the use environment is at a pH above about 5 to 6; it makes the drug-containing composition more hydrophilic so that it readily wets; and it dissolves, lowering the viscosity of the layer rapidly, thus acting as a fluidizing agent. Thus, by accomplishing multiple functions with a single ingredient, additional space is available for the low-solubility drug within the drug-containing composition.

| Properties of Organic Acid Solubilizing Agents | | |
|---|---|---|
| Organic Acid | Equivalents Value (mEq/g) | Water Solubility (mg/mL) |
| Fumaric | 17.2 | 11 |
| Succinic | 16.9 | 110 |

-continued

Properties of Organic Acid Solubilizing Agents

| Organic Acid | Equivalents Value (mEq/g) | Water Solubility (mg/mL) |
| --- | --- | --- |
| Citric | 15.6 | >2000 |
| Malic | 14.9 | 1750 |
| Adipic | 13.7 | 45 |
| Tartaric | 13.3 | 1560 |

For acidic drugs, solubility is increased as pH increases. Exemplary classes of solubilizers for acidic drugs include alkylating or buffering agents and organic bases. It is believed that addition of an alkylating agent or organic base to the dosage form assists in solubilization and hence absorption of the drug. Examples of alkylating or buffering agents include potassium citrate, sodium bicarbonate, sodium citrate, dibasic sodium phosphate, and monobasic sodium phosphate. Examples of organic bases include meglumine, eglumine, monoethanol amine, diethanol amine, and triethanol amine.

The drug-containing composition 14 may optionally include a concentration-enhancing polymer that enhances the concentration of the drug in a use environment relative to control compositions that are free from the concentration-enhancing polymer. The concentration-enhancing polymer should be inert, in the sense that it does not chemically react with the drug in an adverse manner, and should have at least some solubility in aqueous solution at physiologically relevant pHs (e.g. 1-8). Almost any neutral or ionizable polymer that has an aqueous solubility of at least 0.1 mg/mL over at least a portion of the pH range of 1-8 may be suitable. Especially useful polymers are those discussed above for forming solid-amorphous dispersions of the drug with a polymer. Preferred polymers include hydroxypropylmethyl cellulose acetate succinate (HPMCAS), hydroxypropylmethyl cellulose (HPMC), hydroxy propylmethyl cellulose phthalate (HPMCP), cellulose acetate phthalate (CAP), cellulose acetate trimellitate (CAT), and polyvinylpyrrolidone (PVP). More preferred polymers included HPMCAS, HPMCP, CAP and CAT.

Without being bound by any particular theory or mechanism of action, it is believed that the concentration-enhancing polymer prevents or retards the rate at which a drug, delivered from the dosage form and present in the use environment at a concentration greater than its equilibrium value, approaches its equilibrium concentration. Thus, when the dosage form is compared to a control dosage form that is identical except for the absence of the concentration-enhancing polymer, the concentration-enhancing polymer-containing dosage form provides, at least for a short time period, a greater concentration of dissolved drug in the use environment. Appropriate drug forms and concentration-enhancing polymers are discussed in commonly assigned pending patent application "Pharmaceutical Compositions Providing Enhanced Drug Concentrations" filed Dec. 23, 1999 concurrently herewith, U.S. provisional patent application No. 60/171,841, the relevant portions of which are herein incorporated by reference.

The drug-containing composition 14 may optionally include excipients that promote drug stability. Examples of such stability agents include pH control agents such as buffers, organic acids and organic acid salts and organic and inorganic bases and base salts. These excipients can be the same materials listed above for use as solubilizers or fluidizing agents. Another class of stability agents is antioxidants, such as butylated hydroxy toluene (BHT), butylated hydroxyanisole (BHA), vitamin E, and ascorbyl palmitate. The amount of stability agent used in the drug-containing composition should be sufficient to stabilize the low-solubility drug. For pH control agents such as organic acids, the stability agent, when present, may range from 0.1 to 20 wt % of the drug-containing composition. Note that in some formulations, antioxidants such as BHT can lead to discoloration of the dosage form. In these cases, the amount of antioxidant used should be minimized so as to prevent discoloration. The amount of antioxidant used in the drug-containing composition generally ranges from 0 to 1 wt % of the drug-containing composition.

Finally, the drug-containing composition 14 may also include other conventional excipients, such as those that promote performance, tableting or processing of the dosage form. Such excipients include tableting aids, surfactants, water-soluble polymers, pH modifiers, fillers, binders, pigments, osmagents, disintegrants and lubricants. Exemplary excipients include microcrystalline cellulose; metallic salts of acids such as aluminum stearate, calcium stearate, magnesium stearate, sodium stearate, and zinc stearate; fatty acids, hydrocarbons and fatty alcohols such as stearic acid, palmitic acid, liquid paraffin, stearyl alcohol, and palmitol; fatty acid esters such as glyceryl (mono- and di-) stearates, triglycerides, glyceryl (palmitic stearic) ester, sorbitan monostearate, saccharose monostearate, saccharose monopalmitate, and sodium stearyl fumarate; alkyl sulfates such as sodium lauryl sulfate and magnesium lauryl sulfate; polymers such as polyethylene glycols, polyoxyethylene glycols, and polytetrafluoroethylene; and inorganic materials such as talc and dicalcium phosphate. In a preferred embodiment, the drug-containing composition 14 contains a lubricant such as magnesium stearate.

Water-Swellable Composition

Referring again to FIG. 1, the dosage form further comprises a water-swellable composition 16. The water-swellable composition greatly expands as it imbibes water through the coating 18 from the use environment. As it expands, the water-swellable composition increases the pressure within the core 12, causing extrusion of the fluidized drug-containing composition through the port(s) 20 into the environment of use. To maximize the amount of drug present in the dosage form and to ensure that the maximum amount of drug is released from the dosage form so as to minimize residual drug, the water-swellable composition should have a swelling ratio of at least about 2, preferably 3.5, and more preferably 5.

The water-swellable composition 16 comprises a swelling agent in an amount ranging from about 30 to 100 wt % of the water-swellable composition 16. The swelling agent is generally a water-swellable polymer that greatly expands in the presence of water. As discussed above in connection with the swelling agent of the drug-containing composition, the degree of swelling of a swelling agent, or the water-swellable composition itself, can be assessed by measuring its swelling ratio.

Suitable swelling agents for the water-swellable composition are generally hydrophilic polymers that have swelling ratios of about 2.0 or greater. Exemplary hydrophilic polymers include polyoxomers such as PEO, cellulosics such as HPMC and HEC, and ionic polymers. In general, the molecular weight of water swellable polymers chosen for the swelling agent is higher than that of similar polymers used as entraining agents such that, at a given time during drug release, the water-swellable composition 16 after imbibing water tends to be more viscous, less fluid, and more elastic relative to the drug-containing composition 14. In some cases the swelling agent may be even substantially or almost entirely water insoluble such that when partially water swollen during operation, it may constitute a mass of water-swollen elastic particles. Generally, the swelling agent is chosen such that, during operation, the water-swellable composition 16 generally does not substantially intermix with the drug-containing composition 14, at least prior to extruding a majority of the drug-containing composition 14. Thus, for example, when PEO is the swelling agent used in the water-swellable composition 16, a molecular weight of about 800,000 daltons or more is preferred and more preferably a molecular weight of 3,000,000 to 8,000,000 daltons.

A preferred class of swelling agents is ionic polymers, described above for use in various embodiments of the drug-containing composition 14. Exemplary ionic polymer swelling agents include sodium starch glycolate, sold under the trade name EXPLOTAB, croscarmellose sodium, sold under the trade name AC-DI-SOL, polyacrylic acid, sold under the trade name CARBOBOL, and sodium alginate sold under the trade name KELTONE.

The water-swellable composition may optionally further comprise osmotically effective agents, often referred to as "osmogens" or "osmagents." The amount of osmagent present in the water-swellable composition may range from about 0 to about 40 wt % of the water-swellable composition. Typical classes of suitable osmagents are water-soluble salts and sugars that are capable of imbibing water to thereby effect an osmotic pressure gradient across the barrier of the surrounding coating. The osmotic pressure of a material can be calculated using the van't Hoff equation. (See, e.g., *Thermodynamics*, by Lewis and Randall). By "osmotically effective agent" is meant the inclusion of a material with low enough molecular weight, high enough solubility, and sufficient mass in the water-swellable composition that upon imbibing water from the use environment it forms an aqueous solution within the interior of the tablet such that its osmotic pressure exceeds that of the use environment, thereby providing an osmotic pressure driving force for permeation of water from the use environment into the tablet core. Typical useful osmagents include magnesium sulfate, magnesium chloride, calcium chloride, sodium chloride, lithium chloride, potassium sulfate, sodium carbonate, sodium sulfite, lithium sulfate, potassium chloride, sodium sulfate, d-mannitol, urea, sorbitol, inositol, raffinose, sucrose, glucose, fructose, lactose, and mixtures thereof.

In one embodiment of the invention, the water-swellable composition 16 is substantially free from an osmotically effective agent, meaning that there is either a sufficiently small amount of osmagent or that any osmagent present has sufficiently low solubility so as not to increase the osmotic pressure of the water-swellable composition 16 substantially beyond that of the use environment. In order for the dosage form to provide satisfactory release of drug in the absence of an osmagent in the water-swellable composition 16, and when the water-swellable polymer is not an ionic polymer, the dosage form should have a coating that is highly permeable to water. Such high-permeability coatings are described below. When the water-swellable composition 16 is substantially free of an osmotically effective agent, the water swellable composition preferably contains a substantial quantity, typically at least 10 wt % and preferably at least 50 wt %, of a highly swelling polymer such as sodium starch glycolate or sodium croscarmellose. As described earlier, highly swelling materials can be identified by measuring the "swelling ratio" of the material formed into a compact using the method described previously.

The release of a low-solubility drug relatively quickly without the inclusion of an osmagent in the water-swellable composition is a surprising result, since conventional wisdom in the art has held that osmagents should be included in the water-swellable composition to achieve good performance. Circumventing the need for inclusion of an osmagent provides several advantages. One advantage is that the space and weight which would otherwise be occupied by osmagent may be devoted to drug, thus permitting an increase in the amount of drug within the dosage form. Alternatively, the overall size of the dosage form may be decreased. In addition, eliminating the osmagent simplifies the process for manufacture of the dosage form, since the water-swellable composition 16 may omit the step of including an osmagent.

In one embodiment of the invention, the water swellable composition 16 comprises a swelling agent and a tableting aid. The preferred swelling agents (e.g., those that are highly swelling) are difficult to compress to a hardness suitable for use in the dosage form. However, it has been found that adding a tableting aid to the water-swellable composition in the amount of 5 to 50 wt % of the water-swellable composition 16 results in a material that compresses to a hardness suitable for use in the dosage form. At the same time inclusion of a tableting aid can adversely affect the swelling ratio of the water-swellable composition 16. Thus, the quantity and type of tableting aid used must be carefully selected. In general, hydrophilic materials with good compression properties should be used. Exemplary tableting aids include sugars such as lactose, in particular spray-dried versions sold under the trade name FASTFLOW LACTOSE, or xylitol, polymers such as microcrystalline cellulose, HPC, MC or HPMC. Preferred tableting aids are microcrystalline cellulose, both standard grades sold under the trade name AVICEL and silicified versions sold under the trade name PROSOLV and HPC. The amount of tableting aid is chosen to be sufficiently high so that the core 12 compresses well yet sufficiently low so that the water-swellable composition 16 still has a swelling ratio of at least 2, preferably 3.5, more preferably greater than 5. Typically, the amount is at least 20 but less than 60 wt %.

It is further desired that the mixture of swelling agent and tableting aid result in a material that has a "strength" of at least 3 Kiloponds (Kp)/cm$^2$, and preferably at least 5 Kp/cm$^2$. Here, "strength" is the fracture force, also known as the core "hardness," required to fracture a core 12 formed from the material, divided by the maximum cross-sectional area of the core 12 normal to that force. In this test, the fracture force is measured using a Schleuniger Tablet Hardness Tester, model 6D. Both the compressed water-swellable composition 16 and resulting core 12 should have a strength of at least 3 Kp/cm$^2$, and preferably at least 5 Kp/cm$^2$.

In a preferred embodiment, the water-swellable composition 16 comprises a mixture of swelling agents in addition to a tableting aid. For example, the swelling agent croscarmellose sodium can be compressed into a compact with higher strength than the swelling agent sodium starch glycolate. However, the swelling ratio of croscarmellose sodium is lower than that of sodium starch glycolate. A water-swellable composition 16 with the desired combination of high swelling ratio and high strength can be formed using a mixture comprising 15 to 40 wt % sodium starch glycolate, 50 to 70 wt % croscarmellose sodium, and 5 to 20 wt % of the tableting aid microcrystalline cellulose.

The water-swellable composition 16 may also include solubility-enhancing agents or excipients that promote stability, tableting or processing of the dosage form of the same types mentioned above in connection with the drug-containing composition. However, it is generally preferred that such excipients comprise a minor portion of the water-swellable composition 16. In one preferred embodiment, the water-swellable composition 16 contains a lubricant such as magnesium stearate.

The Core

The core 12 may be any known tablet that can be formed by an extrusion or compression process and be subsequently coated and utilized for delivery of drug to a mammal. The tablet can generally range in size from about 1 mm to about 10 cm for its longest dimension. The maximum size of the tablet will be different for different animal species. It can have essentially any shape such that its aspect ratio, defined as the tablet's longest dimension divided by the tablet's shortest dimension, ranges from about 1 to about 5. It is generally preferred that the dimension of the tablet in the direction that the center of mass of the drug-containing layer 14 moves when in the process of being extruded from the dosage form divided by the longest dimension normal to this direction of motion be greater than about 0.5. In addition, the dosage form may comprise two or more relatively small tablets contained in a relatively large container such as a capsule.

Exemplary core 12 shapes are spheres, ellipsoids, cylinders, capsule or caplet shapes and any other known shape. The core 12, following coating, can comprise the entire or a portion of the dosage form. The final dosage form can be for oral, rectal, vaginal, subcutaneous, or other known method of delivery into the environment of use. When the dosage form 10 is intended for oral administration to a human, the core 12 generally has an aspect ratio of about 3 or less, a longest dimension of about 2 cm or less and a total weight of about 1.5 g or less and preferably a total weight of about 1.0 g or less.

To form the dosage form, the ingredients comprising the drug-containing composition 14 and the water-swellable composition 16 are first mixed or blended using processes known in the art. See for example, Lachman, et al., "The Theory and Practice of Industrial Pharmacy" (Lea & Febiger, 1986). For example, a portion of the ingredients of the drug-containing composition 14 can first be blended, then wet granulated, dried, milled, and then blended with additional excipients prior to tableting. Similar processes can be used to form the water-swellable composition.

Once the materials are properly mixed, the core 12 is formed using procedures known in the art, such as compression or extrusion. For example, to form cores in the form of tablets, the desired amount of drug-containing composition 14 is placed in a tablet press and leveled by lightly tamping with the press. The desired amount of water-swellable composition 16 is then added, and the tablet formed by compression. Alternatively, the water-swellable composition may be added to the tablet press first, followed by the drug-containing composition. The amount of force used to compress the tablet core will depend on the size of the dosage form, as well as the compressibility and flow characteristics of the compositions. Typically, a pressure is used that results in a tablet with a strength of 3 to 20 Kp/cm$^2$.

The Coating

Following formation of the core 12, coating 18 is applied. Coating 18 should have both a sufficiently high water permeability that the drug can be delivered within the desired time frame, and high strength, while at the same time be easily manufactured. A water permeability is chosen to control the rate at which water enters the core, thus controlling the rate at which drug is delivered to the use environment. Where a high dose of a low-solubility drug is required, the low solubility and high dose combine to make it necessary to use a high permeability coating to achieve the desired drug release profile while keeping the tablet acceptably small. High strength is required to ensure the coating does not burst when the core swells as it imbibes water, leading to an uncontrolled delivery of the core contents to the use environment. The coating must be easily applied to the dosage form with high reproducibility and yield. Furthermore, the coating must be non-dissolving and non-eroding during release of the drug-containing composition, generally meaning that it be sufficiently water-insoluble that drug is substantially entirely delivered through the delivery port(s) 20, in contrast to delivery via permeation through coating 18.

As described above, the coating 18 is highly water-permeable to allow rapid imbibition of water into core 12 and as a result a rapid release of the drug-containing composition 14. A relative measure of the water permeability of the coating can be made by conducting the following experiment. Finished dosage forms are placed in an open container which is in turn placed in an environmental chamber held at a constant temperature of 40° C. and a constant relative humidity of 75%. The initial rate of weight gain of the dry dosage forms, determined by plotting the weight of the dosage form versus time, divided by the surface area of the dosage form yields a value termed "water flux (40/75)." The water flux (40/75) for a dosage form has been found to be a useful relative measure of the water permeabilities of coatings. For the dosage forms of one embodiment of the present invention, in particular when a rapid release of the drug is desired, the coating should have a water flux (40/75) value of at least $1.0 \times 10^{-3}$ gm/hr·cm$^2$, and preferably at least $1.3 \times 10^{-3}$ gm/hr·cm$^2$.

As mentioned, the coating should also have a high strength to ensure the coating 18 does not burst when the core swells due to imbibition of water from the use environment. A relative measure of coating strength can be made by conducting the following experiment that measures the "durability" of the coating. Finished tablets are placed into an aqueous medium for 10 to 24 hours, allowing the core to imbibe water, swell, and release drug to the media. The swollen dosage form can then be tested in a hardness tester, such as a Model 6D Tablet Tester manufactured by Schleuniger Pharmatron, Inc. The dosage form is placed into the tester so that its delivery port(s) (20) faces one side of the compression plates. The force, in Kp, required to rupture the coating is then measured. The durability of the coating is then calculated by dividing the measured rupture force by the maximum cross-sectional area of the dosage form normal to the applied force. In one embodiment of the present invention, the coating should have a durability of at least 1 Kp/cm$^2$, preferably at least 2 Kp/cm$^2$, and most preferably at least 3 Kp/cm$^2$. Coatings with this or greater durability ensure virtually no burst tablets when the dosage forms are tested in vivo.

Coatings with these characteristics can be obtained using hydrophilic polymers such as plasticized and unplasticized cellulose esters, ethers, and ester-ethers. Particularly suitable polymers include cellulose acetate ("CA"), cellulose acetate butyrate, and ethyl cellulose. A particularly preferred set of polymers are cellulose acetates having acetyl contents of 25 to 42%. A preferred polymer is CA having an acetyl content of 39.8%, and specifically, CA 398-10 manufactured by Eastman of Kingsport, Tenn., having an average molecular weight of about 40,000 daltons. Another preferred CA having an acetyl content of 39.8% is high molecular weight CA having an average molecular weight greater than about 45,000, and specifically, CA 398-30 (Eastman) reported to have an average molecular weight of 50,000 daltons. The high molecular weight CA provides superior coating strength, which allows thinner coatings and thus higher permeability.

Coating is conducted in conventional fashion by first forming a coating solution and then coating by dipping, fluidized bed coating, or preferably by pan coating. To accomplish this, a coating solution is formed comprising the coating polymer and a solvent. Typical solvents useful with the cellulosic polymers noted above include acetone, methyl acetate, ethyl acetate, isopropyl acetate, n-butyl acetate, methyl isobutyl ketone, methyl propyl ketone, ethylene glycol monoethyl ether, ethylene glycol monoethyl acetate, methylene dichloride, ethylene dichloride, propylene dichloride, nitroethane, nitropropane, tetrachloroethane, 1,4-dioxane, tetrahydrofuran, diglyme, and mixtures thereof. A particularly preferred solvent is acetone. The coating solution typically will contain 3 to 15 wt % of the polymer, preferably 5 to 10 wt %, most preferably 7 to 10 wt %.

The coating solution may also comprise pore-formers, non-solvents, or plasticizers in any amount so long as the polymer remains substantially soluble at the conditions used to form the coating and so long as the coating remains water-permeable and has sufficient strength. Pore-formers and their use in fabricating coatings are described in U.S. Pat. Nos. 5,612,059 and 5,698,220, the pertinent disclosures of which are incorporated herein. The term "pore former," as used herein, refers to a material added to the coating solution that has low or no volatility relative to the solvent such that it remains as part of the coating following the coating process but that is sufficiently water swellable or water soluble such that, in the aqueous use environment it provides a water-filled or water-swollen channel or "pore" to allow the passage of water thereby enhancing the water permeability of the coating. Suitable pore-formers include polyethylene glycol (PEG), PVP, PEO, HEC, HPMC and other aqueous-soluble cellulosics, water-soluble acrylate or methacrylate esters, polyacrylic acid and various copolymers and mixtures of these water soluble or water swellable polymers. Enteric polymers such as cellulose acetate phthalate (CAP) and HPMCAS are included in this class of polymers. A particularly preferred pore former is PEG having an average molecular weight from 1000 to 8000 daltons. A particularly preferred PEG is one having a molecular weight of 3350 daltons. The inventors have found that to obtain a combination of high water permeability and high strength when PEG is used as a pore former, the weight ratio of CA:PEG should range from about 6.5:3.5 to about 9:1.

The addition of a non-solvent to the coating solution results in exceptional performance. By "non-solvent" is meant any material added to the coating solution that substantially dissolves in the coating solution and reduces the solubility of the coating polymer or polymers in the solvent. In general, the function of the non-solvent is to impart porosity to the resulting coating. As described below, porous coatings have higher water permeability than an equivalent weight of a coating of the same composition that is not porous and this porosity, when the pores are gas filled, as is typical when the non-solvent is volatile, is indicated by a reduction in the density of the coating (mass/volume). Although not wishing to be bound by any particular mechanism of pore formation, it is generally believed that addition of a non-solvent imparts porosity to the coating during evaporation of solvent by causing the coating solution to undergo liquid-liquid phase separation prior to solidification. As described below for the case of using water as the non-solvent in an acetone solution of cellulose acetate, the suitability and amount of a particular candidate material can be evaluated for use as a non-solvent by progressively adding the candidate non-solvent to the coating solution until it becomes cloudy. If this does not occur at any addition level up to about 50 wt % of the coating solution, it generally is not appropriate for use as a non-solvent. When clouding is observed, termed the "cloud point," an appropriate level of non-solvent for maximum porosity is the amount just below the cloud point. When lower porosities are desired, the amount of non-solvent can be reduced as low as desired. It has been found that suitable coatings can be obtained when the concentration of non-solvent in the coating solution is greater than about 20% of the non-solvent concentration that results in the cloud point.

Suitable non-solvents are any materials that have appreciable solubility in the solvent and that lower the coating polymer solubility in the solvent. The preferred non-solvent depends on the solvent and the coating polymer chosen. In the case of using a volatile polar coating solvent such as acetone or methyl ethyl ketone, suitable non-solvents include water, glycerol, ethylene glycol and its low molecular-weight oligomers (e.g., less than about 1,000 daltons), propylene glycol and its low molecular weight oligomers (e.g., less than about 1,000 daltons), $C_1$ to $C_4$ alcohols such as methanol or ethanol, ethylacetate, acetonitrile and the like.

In general, to maximize its effect, (e.g., formation of pores), the non-solvent should have similar or less volatility than the coating solution solvent such that, during initial evaporation of the solvent during the coating process, sufficient non-solvent remains to cause phase separation to occur. In many cases, where a coating solution solvent such as acetone is used, water is a suitable non-solvent. For acetone solutions comprising 7 wt % CA and 3 wt % PEG, the cloud point at room temperature is at about 23 wt % water. Thus the porosity and in turn the water permeability (which increases with increasing porosity) can be controlled by varying the water concentration up to near the cloud point. For acetone solutions comprising CA and PEG with a total concentration of about 10 wt %, it is desired that the coating solution contain at least 4 wt % water to obtain a suitable coating. When a higher porosity, and thus a higher water permeability is desired (to obtain a faster release rate), the coating solution should contain at least about 15 wt % water.

In one embodiment of the invention, the coating solution is homogeneous, in that when the polymer, solvent, and any pore formers or non-solvents are mixed, the solution comprises a single phase. Typically, a homogenous solution will be clear, and not be cloudy as discussed above.

When using CA 398-10, exemplary coating solution weight ratios of CA:PEG 3350:water are 7:3:5, 8:2:5, and 9:1:5, with the remainder of the solution comprising a solvent such as acetone. Thus, for example, in a solution having a weight ratio of CA:PEG 3350:water of 7:3:5, CA comprises 7 wt % of the solution, PEG 3350 comprises 3 wt % of the solution, water comprises 5 wt % of the solution, and acetone comprises the remaining 85 wt %.

Preferred coatings are generally porous even in the dry state (prior to delivery to the aqueous use environment). By "porous" is meant that the coating has a dry-state density less than the density of the nonporous coating material. By "nonporous coating material" is meant a coating material formed by using a coating solution containing no non-solvent, or the minimum amount of non-solvent required to produce a homogeneous coating solution. The coating in the dry state has a density that is less than 0.9 times, and more preferably less than 0.75 times that of the nonporous coating material. The dry-state density of the coating can be calculated by dividing the coating weight (determined from the weight gain of the tablets before and after coating) by the coating volume (calculated by multiplying the coating thickness, as determined by optical or scanning electron microscopy, by the tablet surface area). The porous nature of the coating is one of the factors that leads to the combination of high water permeability and high strength of the coating.

The coatings may also be asymmetric, meaning that there is a gradient of density throughout the coating thickness. Generally, the outside surface of the coating will have a higher density than the coating nearest the core.

The coating can optionally include a plasticizer. A plasticizer generally swells the coating polymer such that the polymer's glass transition temperature is lowered, its flexibility and toughness increased and its permeability altered. When the plasticizer is hydrophilic, such as polyethylene glycol, the water permeability of the coating is generally increased. When the plasticizer is hydrophobic, such as diethyl phthalate or dibutyl sebacate, the water permeability of the coating is generally decreased.

It should be noted that additives can function in more than one way when added to the coating solution. For example, PEG can function as a plasticizer at low levels while at higher levels it can form a separate phase and act as a pore former. In addition, when a non-solvent is added, PEG can also facilitate pore formation by partitioning into the non-solvent-rich phase once liquid-liquid phase separation occurs.

The weight of the coating around the core depends on the composition and porosity of the coating, the surface to volume ratio of the dosage form, and the desired drug release rate, but generally should be present in an amount ranging from about 3 to 30 wt %, preferably from 8 to 25 wt %, based on the weight of the uncoated core. However, a coating weight of at least about 8 wt % is generally preferred so as to assure sufficient strength for reliable performance, and more preferably a coating greater than about 13 wt %.

While porous coatings based on CA, PEG, and water yield excellent results, other pharmaceutically acceptable materials may be used so long as the coating has the requisite combination of high water permeability, high strength, and ease of manufacture. Further, such coatings may be dense, or asymmetric, having one or more dense layers and one or more porous layers, as described in U.S. Pat. Nos. 5,612,059 and 5,698,220.

The coating 18 must also contain at least one delivery port 20 in communication with the interior and exterior of the coating to allow for release of the drug-containing composition to the exterior of the dosage form. The delivery port can range in size from about the size of the drug particles, and thus could be as small as 1 to 100 microns in diameter and may be termed pores, up to about 5000 microns in diameter. The shape of the port may be substantially circular, in the form of a slit, or other convenient shape to ease manufacturing and processing. The port(s) may be formed by post-coating mechanical or thermal means or with a beam of light (e.g., a laser), a beam of particles, or other high-energy source, or may be formed in situ by rupture of a small portion of the coating. Such rupture may be controlled by intentionally incorporating a relatively small weak portion into the coating. Delivery ports may also be formed in situ by erosion of a plug of water-soluble material or by rupture of a thinner portion of the coating over an indentation in the core. Delivery ports may be formed by coating the core such that one or more small regions remains uncoated. In addition, the delivery port can be a large number of holes or pores that may be formed during coating, as in the case of asymmetric membrane coatings of the type disclosed in U.S. Pat. Nos. 5,612,059 and 5,698,220, the disclosures of which are incorporated by reference. When the delivery pathways are pores there can be a multitude of such pores that range in size from 1 μm to greater than 100 μm. During operation, one or more of such pores may enlarge under the influence of the hydrostatic pressure generated during operation. The number of delivery ports 20 may vary from 1 to 10 or more. At least one delivery port should be formed on the side of the coating that is adjacent to the drug-containing composition, so that the drug-containing composition will be extruded out of the delivery port by the swelling action of the water-swellable composition. It is recognized that some processes for forming delivery ports may also form holes or pores in the coating adjacent to the water-swellable composition. In aggregate, the total surface area of core exposed by delivery ports is less than 5%, and more typically less than 1%.

Other features and embodiments of the invention will become apparent from the following examples which are given for illustration of the invention rather than for limiting its intended scope.

Example 1

Exemplary dosage forms of the present invention were made with a bi-layer core geometry of the type depicted in FIG. 1. The bi-layer core consisted of a drug-containing composition and a water-swellable composition.

To form the drug-containing composition the following materials were blended (see Table A): 35 wt % of the citrate salt of 1-[4-ethoxy-3-(6,7-dihydro-1-methyl-7-oxo-3-propyl-1H-pyrazolo[4,3-d]pyrimidin-5-yl)phenylsulphony]-4-methylpiperazine for treatment of penile erectile disfunction, also known as sildenafil citrate (hereinafter referred to as Drug 1) having a solubility of about 20 μg/mL at pH 6, 30 wt % xylitol (trade name XYLITAB 200), 29 wt % PEO with an average molecular weight of 600,000, 5 wt % sodium starch glycolate (trade name EXPLOTAB), and 1 wt % magnesium stearate. The drug-containing composition ingredients were first combined without the magnesium stearate and blended for 20 minutes in a TURBULA mixer. This blend was pushed through a screen (screen size of 0.065 inch), then blended again for 20 minutes in the same mixer. Next, magnesium stearate was added and the drug-containing composition was blended again for 4 minutes in the same mixer. To form the water-swellable composition, the following materials were blended: 74.5 wt % EXPLOTAB, 25 wt % of the tableting aid silicified microcrystalline cellulose (trade name PROSOLV 90), and 0.5 wt % magnesium stearate. The water-swellable composition was formulated in the same manner as the drug-containing composition.

Tablet cores were formed by placing 400 mg of drug-containing composition in a standard 13/32 inch die and gently leveling with the press. Then, 100 mg water-swellable composition was placed in the die on top of the drug-containing composition. The tablet core was then compressed to a hardness of about 11 Kp. The resulting bi-layer tablet core had a total weight of 500 mg and contained a total of 28 wt % Drug 1 (140 mg), 24 wt % XYLITAB 200, 23 wt % PEO 600,000, 18.9 wt % EXPLOTAB, 5 wt % PROSOLV 90, and 1.1 wt % magnesium stearate.

Coatings were applied by a Vector LDCS-20 pan coater. The coating solution contained CA (CA 398-10 from Eastman Fine Chemical, Kingsport, Tenn.), polyethylene glycol (PEG 3350, Union Carbide), water, and acetone in a weight ratio of 7/3/5/85 (wt %). The flow rate of the inlet heated drying air of the pan coater was set at 40 ft$^3$/min with the outlet temperature set at 25° C. Nitrogen at 20 psi was used to atomize the coating solution from the spray nozzle, with a nozzle-to-bed distance of 2 inches. The pan rotation was set to 20 rpm. The so-coated tablets were dried at 50° C. in a convection oven. The final dry coating weight amounted to 40.5 mg or 8.1 wt % of the tablet core. Five 900 μm diameter holes were then mechanically drilled in the coating on the drug-containing composition side of the tablet to provide 5 delivery ports per tablet. Table C summarizes the characteristics of the dosage form.

To simulate in vivo drug dissolution, tablets were placed in 900 mL of a simulated gastric solution (10 mM HCl, 100 mM NaCl, pH 2.0, 261 mOsm/kg) for 2 hours, then transferred to 900 mL of a simulated intestinal environment solution (6 mM $KH_2PO_4$, 64 mM KCl, 35 mM NaCl, pH 7.2, 210 mOsm/kg), both solutions being stirred at 50 rpm. A residual dissolution test was performed as described in the Detailed Description section. Residual drug was analyzed by HPLC using a Waters Symmetry $C_{18}$ column. The mobile phase consisted of 0.05 M triethanolamine (pH 3)/methanol/acetonitrile in a volume ratio of 58/25/17. Drug concentration was calculated by comparing UV absorbance at 290 nm to the absorbance of Drug 1 standards. The amount of drug remaining in the tablets was subtracted from the total initial amount of drug in the tablet to obtain the amount released at each time interval. Results are shown in Table 1 and summarized in Table D.

TABLE 1

| Time (hours) | Drug (wt % released) |
|---|---|
| 0 | 0 |
| 2 | 25 |
| 4 | 46 |
| 8 | 74 |
| 14 | 94 |
| 20 | 98 |

The data show that 25 wt % of the drug was released within 2 hours, 74 wt % within 8 hours, and 98 wt % of the drug was released within 20 hours. Thus, the present invention provided a rapid release of over 70 wt % within 8 hours and very low residual value at 20 hours of a relatively high dose (140 mg) of a low-solubility drug in a relatively low mass (540 mg) dosage form.

Example 2

This example demonstrates the inventive delivery of a high dose of Drug 1 from bi-layer tablets by increasing the amount of drug in the drug-containing composition. For the tablets of Example 2, the drug-containing composition consisted of 56 wt % Drug 1, 20 wt % XYLITAB 200, 19 wt % PEO with an average molecular weight of 600,000, 4 wt % EXPLOTAB, and 1 wt % magnesium stearate. The water-swellable composition consisted of 74.5 wt % EXPLOTAB, 25 wt % PROSOLV 90, and 0.5 wt % magnesium stearate. These tablets were made as in Example 1, except that 500 mg of the drug-containing composition was used to make the tablet. See Table C for further details of the make-up of the tablets. The drug-containing composition and water-swellable composition for this example were combined in a ratio of 83.3 wt % drug-containing composition to 16.7 wt % water-swellable composition. Dissolution tests were performed as described in Example 1. Results are shown in Table 2 and summarized in Table D.

TABLE 2

| Time (hours) | Drug (wt % released) |
|---|---|
| 0 | 0 |
| 2 | 16 |
| 4 | 34 |
| 8 | 57 |
| 14 | 76 |
| 20 | 86 |

The above data show that 16 wt % of the drug was released within 2 hours and 86 wt % within 20 hours. Thus, the dosage forms of the present invention performed well, even with a high drug loading in the drug-containing composition.

Examples 3A-3B

These examples demonstrate the inventive delivery of various drugs from bi-layer tablets. For the tablets of Example 3A, the drug-containing composition consisted of 35% sertraline HCl (Drug 2) having a solubility of 0.2 mg/mL at pH 7, 30 wt % XYLITAB 200, 28.75 wt % PEO with an average molecular weight of 600,000, 5 wt % EXPLOTAB, and 1.25 wt % magnesium stearate. The water-swellable composition consisted of 74.5 wt % EXPLOTAB, 25 wt % PROSOLV 90, and 0.5 wt % magnesium stearate. These tablets were made as in Example 1. Dissolution tests were performed on these tablets in the same manner as Example 1 except the residual drug was analyzed by HPLC using a Phenomenex Ultracarb 5 ODS 20 column. The mobile phase consisted of 35 vol % TEA-acetate buffer (3.48 mL triethanolamine and 2.86 mL glacial acetic acid in 1 L HPLC $H_2O$) in acetonitrile. Drug concentration was calculated by comparing UV absorbance at 230 nm to the absorbance of sertraline standards. The results are presented in Table 3 and summarized in Table D.

For the tablets of Example 3B, the drug-containing composition consisted of 32.4 wt % of mesylate salt of the drug 4-[3-[4-(2-methylimidazol-1-yl)phenylthio]phenyl]-3,4,5,6-tetrahydro-2H-pyran-4-carboxamide hemifumarate a 5-lipoxygenase inhibitor for the treatment of chronic inflammatory conditions such as asthma (Drug 3) having a solubility of 3.7 mgA/mL at pH 4, 31.2 wt % XYLITAB 200, 29.9 wt % PEO with an average molecular weight of 600,000, 5.2 wt % EXPLOTAB, and 1.3 wt % magnesium stearate (see Table A). The water-swellable composition consisted of 74.5 wt % EXPLOTAB, 24.5 wt % PROSOLV 90, and 1 wt % magnesium stearate. These tablets were made as in Example 1. Dissolution tests were performed on these tablets in accordance with Example 1 with the following exceptions: residual drug was analyzed by dissolving tablets in 0.1 N HCl and measuring UV absorbance at 258 nm. Results are shown in Table 3 and summarized in Table D.

TABLE 3

| Example | Time (hours) | Drug (% released) |
|---|---|---|
| 3A | 0 | 0 |
|  | 2 | 22 |
|  | 4 | 45 |
|  | 8 | 79 |
|  | 14 | 92 |
|  | 20 | 94 |
| 3B | 0 | 0 |
|  | 2 | 18 |
|  | 4 | 38 |
|  | 8 | 68 |

TABLE 3-continued

| Example | Time (hours) | Drug (% released) |
| --- | --- | --- |
| | 12 | 85 |
| | 18 | 89 |
| | 24 | 91 |

Examples 3A and 3B show low residual drug after 24 hours with virtually no lag time. Along with Example 1, these examples show that different low-solubility drugs can be successfully delivered from dosage forms of this invention.

Example 4

This example demonstrates the inventive delivery of Drug 2 from bi-layer tablets without an ionic swelling agent in the water-swellable composition. For the tablets of Example 4, the drug-containing composition consisted of 35% Drug 2, 30 wt % XYLITAB 200, 29 wt % PEO with an average molecular weight of 600,000, 5 wt % EXPLOTAB, and 1 wt % magnesium stearate (see Table A). The water-swellable composition consisted of 65 wt % PEO with an average molecular weight of 5,000,000, 29.4 wt % NaCl, 5% of the tableting aid hydroxymethylcellulose (METHOCEL), and 0.6 wt % magnesium stearate (see Table B). These tablets were made as in Example 1, except that 490 mg of the drug-containing composition and 245 mg of the water-swellable composition were used to make the tablet (see Table C). Dissolution tests were performed on these tablets as described in Example 3A. Results are shown in Table 4 and summarized in Table D.

TABLE 4

| Time (hours) | Drug (wt % released) |
| --- | --- |
| 0 | 0 |
| 1 | 1 |
| 2 | 15 |
| 4 | 47 |
| 8 | 80 |
| 12 | 90 |
| 18 | 95 |
| 24 | 87 |

The data show that 15 wt % of the drug was released within 2 hours and 87 wt % was released within 24 hours when there was no ionic swelling agent in the water-swellable composition.

Examples 5A-5C

These examples demonstrate that various amounts of ionic swelling agent and tableting aid can be used to form dosage forms with the desired release profile.

For the tablets of Examples 5A, 5B, and 5C, the drug-containing composition consisted of 35 wt % Drug 1, 30 wt % XYLITAB 200, 29 wt % PEO with an average molecular weight of 600,000, 5 wt % EXPLOTAB, and 1 wt % magnesium stearate. The drug-containing composition was wet-granulated using deionized water and dried overnight in a 40° C. oven. For tablets of Example 5A, the water-swellable composition consisted of 74.35 wt % EXPLOTAB, 24.85 wt % PROSOLV 90, 0.3 wt % Red Lake #40, and 0.3 wt % magnesium stearate. The water-swellable composition was formed by wet-granulating the EXPLOTAB and PROSOLV 90 using water as solvent, drying this mixture, and then blending with the other ingredients.

For tablets of Example 5B, the water-swellable composition consisted of 49.4 wt % EXPLOTAB, 49.4 wt % PROSOLV 90, 0.2 wt % Red Lake #40, and 1 wt % magnesium stearate. The water-swellable composition was wet-granulated as in Example 5A.

For tablets of Example 5C, the water-swellable composition consisted of 59.35 wt % EXPLOTAB, 39.4 wt % PROSOLV 90, 0.25 wt % Red Lake #40, and 1 wt % magnesium stearate. The water-swellable composition was wet-granulated as in Example 5A.

Tablets were formed by placing 400 mg of drug-containing composition in a standard 13/32 inch die and tamping lightly. Then, 100 mg water-swellable composition was placed in the die on top of the drug-containing composition. The tablet was then compressed to a hardness of about 12 Kp. All cores were coated in the same manner as in Example 1, except the final dry coating weights for each example were 40.5 mg (8.1 wt %) for 5A, 46.5 mg (9.3 wt %) for 5B, and 43.5 mg (8.7 wt %) for 5C respectively.

Dissolution tests were performed on these tablets as described in Example 1. Results are shown in Table 5 and summarized in Table D.

TABLE 5

| Example | Time (hours) | Drug (wt % released) |
| --- | --- | --- |
| 5A EXPLOTAB/ PROSOLV 90 = 75/25* | 0 | 0 |
| | 2 | 15 |
| | 4 | 43 |
| | 8 | 69 |
| | 14 | 94 |
| | 20 | 97 |
| 5B EXPLOTAB/ PROSOLV 90 = 50/50* | 0 | 0 |
| | 2 | 15 |
| | 4 | 40 |
| | 8 | 67 |
| | 14 | 89 |
| | 20 | 96 |
| 5C EXPLOTAB/ PROSOLV 90 = 60/40* | 0 | 0 |
| | 2 | 16 |
| | 4 | 40 |
| | 8 | 69 |
| | 14 | 89 |
| | 20 | 96 |

*approximate

The data show that the weight ratio of EXPLOTAB to PROSOLV 90 can be varied from about 75/25 to about 50/50 without any adverse effect on the desired drug release profile.

Example 6

This example demonstrates that low residual drug values may be obtained with the dosage forms of the invention even with high drug loading. For the tablets of Example 6, the drug-containing composition and the water-swellable composition were the same as in Example 2, and were made as in Example 2, except that 200 mg of the water-swellable composition was used to make the tablets (71.4% drug-containing composition/28.6% water-swellable composition) and the tablets had a 77.7 mg (11.1 wt %) coating. Dissolution tests were performed as described in Example 1. Results are shown in Table 6.

TABLE 6

| Time (hours) | Drug (wt % released) |
| --- | --- |
| 0 | 0 |
| 2 | 16 |
| 4 | 39 |
| 8 | 65 |
| 14 | 89 |
| 20 | 94 |

A comparison of these data with those of Example 2 show that the initial rate of drug release was the same, releasing 16 wt % of the drug within 2 hours. Compared to Example 2, the data also show that increasing the amount of water-swellable composition in the core (Example 6) resulted in a higher percentage (94% vs. 86%) of the drug being released after 20 hours, thereby leaving a lower amount of residual drug.

Examples 7A-7D

These examples demonstrate the relationship between the drug release profile and the water permeability of the coating. For the tablets of Examples 7A, 7B, 7C, and 7D, the drug-containing composition consisted of 35 wt % Drug 1, 30 wt % XYLITAB 200, 29 wt % PEO with an average molecular weight of 600,000, 5 wt % EXPLOTAB, and 1 wt % magnesium stearate. The water-swellable composition consisted of 74.35 wt % EXPLOTAB, 24.85 wt % PROSOLV 90, 0.3 wt % Red Lake #40, and 0.3 wt % magnesium stearate.

These tablets were made as in Example 1, except that the tablets had different amounts of coating (see Table C). For the tablets of Example 7A, the coating had a final dry weight of 29 mg (5.8 wt %). For the tablets of Example 7B, the coating had a final dry weight of 56.5 mg (11.3 wt %). For the tablets of Example 7C, the coating had a final dry weight of 89.5 mg (17.9 wt %). For the tablets of Example 7D, the coating had a final dry weight of 124.5 mg (24.9 wt %). Generally, the thicker the coating, the lower the expected water permeability. Dissolution tests were performed on these tablets as described in Example 1. Results are shown in Table 7 and are summarized in Table D.

TABLE 7

| Example | Time (hours) | Drug (wt % released) |
| --- | --- | --- |
| 7A | 0 | 0 |
| | 2 | 30 |
| | 4 | 57 |
| | 8 | 88 |
| | 14 | 98 |
| | 20 | 97 |
| 7B | 0 | 0 |
| | 2 | 19 |
| | 4 | 45 |
| | 8 | 69 |
| | 14 | 94 |
| | 20 | 98 |
| 7C | 0 | 0 |
| | 2 | 8 |
| | 4 | 27 |
| | 8 | 60 |
| | 14 | 82 |
| | 20 | 94 |
| 7D | 0 | 0 |
| | 2 | 0 |
| | 4 | 17 |
| | 8 | 48 |
| | 14 | 68 |
| | 20 | 88 |

Examples 7A-7D show that as the water permeability decreased, i.e., as the coating weight increased, the rate of drug release decreased. The data show that as the coating thickness increased, the fraction of drug delivered between 0 and 2 hours decreased, while the fraction of drug delivered from 8 to 20 hours increased.

Example 8

This example demonstrates the delivery of an amorphous dispersion of Drug 2 in a concentration-enhancing polymer from a dosage form of the invention. Amorphous solid dispersions of Drug 2 in HPMCP were prepared by spray-drying a solution containing 0.65 wt % sertraline free base, 0.65 wt % hydroxy propylmethyl cellulose phthalate (HPMCP 55), 49.35 wt % methanol, and 49.35 wt % acetone. The drug was dissolved in the methanol, and the polymer was dissolved in the acetone, before combining the solutions. The solution was spray-dried using a two-fluid external mix spray nozzle at 1.8 bar at a feed rate of 187 to 211 g/min into the stainless steel chamber of a Niro spray-dryer, maintained at a temperature of 230° C. at the inlet and 72° C. at the outlet.

To form the drug-containing composition, the following materials were blended: 41.15 wt % sertraline dispersion (1:1 sertraline free base:HPMCP), 26.75 wt % PEO having an average molecular weight of 600,000, 26.75 wt % XYLITAB 200, 4.33 wt % EXPLOTAB, and 1.02 wt % magnesium stearate. The drug-containing composition ingredients were combined and precompressed, then milled in a co-mill at 1100 rpm with a screen size having 0.075-inch openings.

To form the water-swellable composition, the following materials were blended: 74.66 wt % EXPLOTAB, 24.73 wt % PROSOLV 90, 0.47 wt % magnesium stearate, and 0.14 wt % Red Lake #40. The water-swellable composition ingredients were combined without the magnesium stearate, blended 20 minutes in a Turbula mixer, then blended again for 4 minutes with magnesium stearate. Assays of these tablets confirmed 112 mg of active sertraline (mgA).

Release of the sertraline dispersion from the bi-layer tablets into simulated intestinal buffer was measured by HPLC as described in Example 3A. Results are shown in Table 8 and summarized in Table D.

TABLE 8

| Time (hours) | Drug (wt % released) |
| --- | --- |
| 0 | 0 |
| 1 | 7 |
| 2 | 17 |
| 4 | 40 |
| 8 | 68 |
| 12 | 86 |
| 18 | 91 |
| 24 | 86 |

The data demonstrate satisfactory delivery of a sertraline dispersion from dosage forms of this invention.

Example 9

This example illustrates the delivery of another drug dispersion from a bi-layer tablet. The drug was in the form of a solid amorphous dispersion comprising 50 wt % of 5-chloro-1H-indole-2-carboxylic acid [(1S)-benzyl-3-((3R,4S)-dihydroxypyrrolidin-1-yl-)-(2R)-hydroxy-3-oxypropyl]amide (a glycogen phosphorylase inhibitor) (Drug 4) having a water solubility of 80 μg/mL and 50% hydroxy propylmethyl cellulose acetate succinate (HPMCAS MF grade). The solid dispersion was prepared in essentially the same way as Example 8 except as follows: the solution comprised 7.5 wt % Drug 4, 7.5 wt % polymer and 85 wt % 95:5 acetone:$H_2O$ (wt:wt). This solution was spray-dried using an external mix 2-fluid atomizer with feed rates of 460 g/min atomizing gas and 200 g/min solution feed with an inlet temperature of 195° C. and an outlet temperature of 70° C.

The resulting solid particles had an average diameter of approximately 50 µm. The drug-containing composition consisted of 44.4 wt % solid dispersion, 26.1 wt % XYLITAB 200, 25.2 wt % PEO with an average molecular weight of 600,000, 3.5 wt % EXPLOTAB, and 0.8 wt % magnesium stearate. The water-swellable composition consisted of 74.8 wt % EXPLOTAB, 24.8 wt % PROSOLV 90, and 0.4 wt % magnesium stearate (see Table B).

The drug-containing composition ingredients were mechanically mixed until substantially homogeneous, compressed into a weak tablet, then the resulting tablets were ground to particles less than 16 mesh in size. The water-swellable composition ingredients were then mixed until substantially homogeneous. Tablets were formed by first placing 450 mg of ground drug-containing composition in an f-press in a standard $^{15}\!/_{32}$-inch die and tamping lightly. Then, 150 mg of the water-swellable composition mixture was placed in the die on top of the drug-containing composition. The tablet was then compressed to a hardness of 15 Kp.

The resulting bi-layer tablet core had a total weight of 600 mg and contained 199.8 mg of solid dispersion, 99.9 mg of which was Drug 4. This core was then coated as in Example 1 to obtain a coating weight of 8.9%, and five 900 µm holes were drilled on the drug face only of the tablet.

The dissolution of drug was studied by placing the bi-layer tablets in intestinal buffer and stirring at 50 rpm. Tablets were dissolved in 75/25 methanol/water for residual analysis. Drug concentration over time was determined using a Zorbax SB C18 column, with a mobile phase of 35 vol % acetonitrile in water, and UV absorbance measured at 297 nm. The results are shown in Table 9 and are summarized in Table D.

The data shows satisfactory release of a dispersion of Drug 4 from the bi-layer tablet.

TABLE 9

| Time (hours) | Drug (wt % released) |
|---|---|
| 0 | 0 |
| 1 | 1 |
| 2 | 4 |
| 4 | 28 |
| 8 | 63 |
| 12 | 81 |
| 18 | 96 |
| 24 | 97 |

Example 10

This example illustrates the delivery of 5-(2-(4-(3-benzisothiazolyl)-piperazinyl)ethyl-6-chlorooxindole (Drug 5) from a bi-layer tablet. The drug was in the form of a solid dispersion comprising 10 wt % of Drug 5 having a solubility of 3 µg/mL in model fasted duodenal solution and 90 wt % HPMCAS, HF grade. The solid dispersion was prepared in essentially the same way as Example 8 except as follows: the solution comprised 0.3 wt % Drug 5, 2.7 wt % HPMCAS and 97 wt % MeOH. This solution was spray dried at 19 psi and a 140 g/min feed rate with an inlet temperature of 264° C. and an outlet temperature of 62° C.

The drug-containing composition consisted of 45.1 wt % solid dispersion, 25 wt % XYLITAB 200, 25 wt % PEO with an average molecular weight of 600,000, 3.9 wt % EXPLOTAB, and 1% magnesium stearate. The water-swellable composition consisted of 74.8 wt % EXPLOTAB, 24.7 wt % PROSOLV 90, and 0.5 wt % magnesium stearate. Tablets were formed by first mechanically mixing the above drug-containing composition ingredients until homogeneous, compressing into a tablet of 10-20 Kp, and grinding resulting tablets to particles. The above water-swellable composition ingredients were mixed until homogeneous. Bi-layer tablets were prepared from the drug-containing composition particles and water-swellable composition, as described in Example 9.

The resulting bi-layer core had a total weight of 700 mg and contained 247.8 mg of solid dispersion, 22.84 mg of which was Drug 5. The bi-layer core was then coated as in Example 1 to obtain a coating weight of 11.3%, and five 2 mM holes were drilled.

The dissolution of drug was studied by placing the bi-layer tablets in intestinal buffer and stirring at 50 rpm. Tablets were dissolved in 75/25 methanol/water (w/w) for analysis for residual drug content. Drug concentration was determined using HPLC, with a mobile phase of 60 vol % 0.02 M $KH_2PO_4$, pH 3.0 in ACN, and diode array detection at 254 nm. The results are shown in Table 10 and summarized in Table D.

TABLE 10

| Time (hours) | Drug (wt % released) |
|---|---|
| 0 | 0 |
| 1 | 5 |
| 2 | 13 |
| 4 | 26 |
| 8 | 46 |
| 12 | 73 |
| 18 | 76 |
| 24 | 74 |

The data shows satisfactory release of a dispersion of Drug 5 from the bi-layer tablet.

Example 11

This example demonstrates the inventive delivery of Drug 2 from bi-layer tablets without a swelling agent in the drug-containing composition. For the tablets of Example 11, the drug-containing composition consisted of 22.8% Drug 2, 71.7 wt % PEO with an average molecular weight of 200,000, 5 wt % Methocel, and 0.5 wt % magnesium stearate. The water-swellable composition consisted of 74.5 wt % EXPLOTAB, 25.0 wt % PROSOLV 90, and 0.5 wt % magnesium stearate. These tablets were made as in Example 1, except that 490 mg of the drug-containing composition and 245 mg of the water-swellable composition were used to make the tablet. Dissolution tests were performed on these tablets as described in Example 1. Results are shown in Table 11 and summarized in Table D.

TABLE 11

| Time (hours) | Drug (wt % released) |
|---|---|
| 0 | 0 |
| 1 | 3 |
| 2 | 17 |
| 4 | 49 |
| 8 | 70 |
| 12 | 84 |
| 20 | 88 |
| 24 | 92 |

The data show that satisfactory drug delivery was obtained with dosage forms of the invention without a swelling agent in the drug-containing composition.

Example 12

This example describes the results of tests to determine the swelling volume of swelling agents that may be used in the formulation of the water-swellable composition.

The following experiment was used to determine the swelling ratio of materials. The materials were first blended and then 500 mg of the material was compressed into a tablet using a ¹³⁄₃₂-inch die, the tablet having a strength ranging from 3 to 16 Kp/cm². This compressed material was then placed into a glass cylinder of approximately the same inside diameter as the tablet. The height of the tablet was then measured. Using this height and the diameter of the tablet, the volume of the dry material was determined. Next, the glass cylinder was filled with test media of either deionized water, simulated intestinal buffer, or simulated gastric buffer. The glass cylinder and test media were all equilibrated at a constant temperature of 37° C. As the materials in the tablet absorbed water, the height of the tablet increased. At each time interval, the height of the tablet was measured, from which the volume of the swollen tablet was determined. The ratio of the volume of the tablet after reaching a constant height to that of the volume of the dry tablet is the swelling ratio of the material. The results of these tests are shown in Table 12.

TABLE 12

| Water-Swellable Composition | | | Swelling Ratio (v/v) | | |
|---|---|---|---|---|---|
| Swelling Agent | Tableting Aid/ Additive | Swelling Agent/ Tableting Aid (w/w) | Gastric Buffer | Intestinal Buffer | Water |
| PEO 5,000,000 | NONE | 100/0 | 2.4 | 2.4 | 2.4 |
| PEO 5,000,000 | Microcrystalline cellulose[1] | 85/15 | 2.2 | 2.1 | 2.4 |
| PEO 5,000,000 | Microcrystalline cellulose | 70/30 | 2.0 | 2.1 | 2.4 |
| PEO 5,000,000 | Microcrystalline cellulose | 50/50 | 2.0 | 1.9 | 1.9 |
| PEO 5,000,000 | NaCl | 70/30 | 2.6 | 2.6 | 2.8 |
| PEO 2,000,000 | Microcrystalline cellulose | 85/15 | 2.8 | 2.8 | 3.0 |
| Polyacrylic acid[2] | Silicified microcrystalline cellulose[3] | 70/30 | 1.9 | 1.5 | |
| Polyacrylic acid | Microcrystalline cellulose | 50/50 | 1.8 | 1.7 | |
| Sodium croscarmelose[4] | None | 100/0 | 7.0 | 5.4 | 7.1 |
| Sodium croscarmellose | Microcrystalline cellulose | 85/15 | 7.1 | 5.9 | 7.2 |
| Sodium croscarmellose | Microcrystalline cellulose | 70/30 | 5.5 | 6.3 | 5.5 |
| Sodium croscarmellose | Microcrystalline cellulose | 50/50 | 4.6 | 5.3 | 5.7 |
| Sodium starch glycolate[5] | Microcrystalline cellulose | 50/50 | 7.1 | 7.7 | 25.2 |
| Sodium starch glycolate | Microcrystalline cellulose | 70/30 | 9.0 | 9.6 | 26.8 |
| Sodium starch glycolate | Microcrystalline cellulose | 85/15 | 10.9 | 11.9 | 34.7 |
| Sodium starch glycolate | Silicified Microcrystalline cellulose | 50/50 | 7.9 | 8.7 | |
| Sodium starch glycolate | Silicified Microcrystalline cellulose | 75/25 | 7.4 | 9.1 | 14.4 |
| Sodium starch glycolate | Silicified Microcrystalline cellulose | 70/30 | 10.6 | 11.2 | |
| Sodium starch glycolate | Hydroxypropyl cellulose[6] | 98/2 | — | | 17.2 |
| Sodium starch glycolate | Hydroxypropyl cellulose | 95/5 | 5.6 | | 8.4 |
| Sodium starch glycolate | Hydroxypropyl cellulose | 90/10 | 7.2 | | 6.9 |
| Sodium starch glycolate | Hydroxypropyl cellulose | 85/15 | — | 3.8 | 3.8 |
| Sodium starch glycolate | Hydroxypropyl cellulose | 70/30 | 3.7 | 3.9 | 3.3 |
| Sodium starch glycolate | Hydroxypropyl cellulose | 50/50 | 2.4 | 2.5 | 2.4 |
| Sodium alginate[7] | Silicified microcrystalline cellulose | 50/50 | 2.7 | 2.9 | |
| Hydroxyethyl cellulose[8] | NONE | 100/0 | 2.8 | 2.8 | 2.7 |
| Hydroxyethyl cellulose | Microcrystalline cellulose | 50/50 | 2.4 | 2.1 | 2.5 |

[1] = AVICEL
[2] = CARBOPOL 974PNF
[3] = PROSOLV 90
[4] = AC-DI-SOL
[5] = EXPLOTAB
[6] = Klucel
[7] = Keltone LVCR
[8] = Natrosol

Example 13

Exemplary dosage forms of the present invention were made with a bi-layer core geometry of the type depicted in FIG. 1. This example illustrates dosage forms of this invention which release drug over a short duration, utilizing a durable, high permeability coating. The drug-containing composition comprised the following materials: 22.8 wt % Drug 2, 71.7 wt % PEO with an average molecular weight of 200,000 (Polyox WSR N80), 5.0 wt % METHOCEL K3 LV Prem (a tablet binder), and 0.5 wt % of the lubricant, magnesium stearate.

To form the drug-containing composition, the ingredients (without the magnesium stearate) were blended for 20 minutes in a Turbula mixer. This blend was screened through a 0.065-inch screen, then blended again for 20 minutes. Next, magnesium stearate was added and the materials were blended again for 4 minutes. The water-swellable composition comprised the following materials: 65.0 wt % PEO with an average molecular weight of 5,000,000 (Polyox WSR Coagulant), 29.3 wt % sodium chloride, 5.1 wt % METHOCEL K3 LV Prem., and 0.6 wt % magnesium stearate.

To form the water-swellable composition, the ingredients (without the magnesium stearate) were blended 20 minutes in a Turbula mixer, then blended again for 4 minutes with magnesium stearate.

The drug-containing composition and the water-swellable composition were tableted together using direct compression. A portion of the drug-containing composition (490 mg) was placed in an f-press with a standard round concave $^{15}/_{32}$-inch die, then gently leveled with the upper punch. A 245 mg portion of the water-swellable composition was placed on top of this and the tablet compressed. The compression distance between the upper and lower punches on the f-press was adjusted until the hardness of the resulting tablets measured 15 Kp. The resulting bi-layer tablet contained a total of 15.2 wt % Sertraline HCl, 47.8 wt % PEO 200,000, 5.0 wt % METHOCEL, 0.5 wt % magnesium stearate, 21.7 wt % PEO 5,000,000, and 9.8 wt % sodium chloride. Assays of these tablets confirmed 112 mg of Sertraline HCl, or 100 mg of active Sertraline (mgA).

The tablets were coated with a high water permeability coating in a Vector LDCS-20 pan coater as described in Example 1. The coating solution contained cellulose acetate (CA 398-10), polyethylene glycol (PEG 3350), water, and acetone in a weight ratio of 7/3/5/85. Heated drying air (40 cfm) was adjusted to maintain the pan coater outlet temperature at 25° C. Nitrogen at 20 psi was used to atomize the coating solution from the spray nozzle, with a nozzle-to-bed distance of 2 inches. The pan tumbled at 20 rpm. The final dry coating weight amounted to 12.9 wt % of the weight of the tablet core. One 900-μm hole was hand-drilled on the face of the tablet. The total weight of the coated tablet was 830 mg.

An in vitro residual test was performed as described in Example 3A. Results are shown in Table 13 and are summarized in Table D. The data show that 19% of the drug was released within 2 hours, and that 98% of the drug was released within 8 hours. Observations of the tablets during the release test indicated that the coating was able to withstand the swelling of the PEO-based core and remained intact for the duration of the test.

TABLE 13

| Time (hours) | Drug (wt % released) |
| --- | --- |
| 0 | 0 |
| 1 | 2 |
| 2 | 19 |
| 4 | 51 |
| 8 | 98 |
| 12 | 99 |

TABLE 13-continued

| Time (hours) | Drug (wt % released) |
| --- | --- |
| 18 | 99 |
| 24 | 99 |

Example 14

This example demonstrates the inventive delivery of Drug 2 from a tablet of the present invention, while increasing the percentage of drug in the drug-containing composition to 35 wt %. Tablets for Example 14 were made as in Example 13, with ingredients indicated in Tables A, B, and C. Dissolution tests were performed as described in Example 3A. Results are shown in Table 14 and summarized in Table D.

TABLE 14

| Time (hours) | Drug (wt % released) |
| --- | --- |
| 0 | 0 |
| 1 | 7 |
| 2 | 25 |
| 4 | 65 |
| 8 | 97 |
| 12 | 98 |
| 18 | 98 |
| 24 | 98 |

The data show that even with a high percentage of drug in the drug-containing composition, the rate of drug release remained high, showing a release of 25% after 2 hours. Furthermore, 97% of the drug had been released within 8 hours. This example shows that successful delivery of drug from dosage forms of this invention can be obtained, even for delivery of large amounts of drug as a percentage of the drug-containing composition. Such high drug loadings are desirable when delivery of a high dose of drug is desired while keeping tablet size acceptably small.

Examples 15A-C

These examples show the effects of the formulation of the coating material on the water permeability of the coating by measuring the water flux (40/75), a relative measure of the water permeability of coatings useful in comparing coatings. Tablets were made as in Example 13, with the exceptions noted in Tables A, B, and C. The tablets were made using $^{15}/_{32}$-inch tooling, with compression at 13.4 Kp. Each tablet had a surface area of approximately 4.35 cm$^2$.

Coatings were applied to these tablets as in Example 1. Table 15.1 reports the composition of the coating solutions used. Acetone was used as the solvent in all cases.

TABLE 15.1

| Example | Coating Solution Formulation (wt %) | | | Coating Weight per Tablet | |
| --- | --- | --- | --- | --- | --- |
| | CA 398-10 | PEG | Water | mg | wt % |
| 15A | 7 | 3 | 5 | 82 | 11.2 |
| 15B | 8 | 2 | 5 | 84 | 11.4 |
| 15C | 9 | 1 | 5 | 86 | 11.7 |

To determine water flux (40/75) values, five tablets from each example were placed in a weigh boat in an environmental chamber having a constant temperature of 40° C. and a constant relative humidity of 75%. Periodically, the tablets were removed and weighed. Table 15.2 gives the data from this experiment.

TABLE 15.2

| | Weight of 5 Tablets (g) | | |
|---|---|---|---|
| Time (Hours) | Example 15A | Example 15B | Example 15C |
| 0 | 4.0241 | 4.0383 | 4.0703 |
| 0.5 | 4.0491 | 4.0590 | 4.0867 |
| 1 | 4.0611 | 4.0676 | 4.0948 |
| 3 | 4.0882 | 4.0901 | 4.1158 |
| 4 | 4.0943 | 4.0966 | 4.1213 |
| 5 | 4.1025 | 4.1031 | 4.1281 |
| 6 | 4.1082 | 4.1076 | 4.1338 |
| 7 | 4.1119 | 4.1110 | 4.1370 |
| 22 | 4.1338 | 4.1303 | 4.1593 |
| 23 | 4.1374 | 4.1341 | 4.1627 |
| 24 | 4.1406 | 4.1356 | 4.1649 |

The water flux (40/75) values of the coatings were determined by dividing the initial slope obtained by plotting weight versus time by the tablet surface area for 5 tablets. Table 15.3 reports the results of these calculations (using a linear regression fit of the first three data points to determine the initial slope. The data show that the water flux (40/75) values increased as the amount of PEG included in the coating solution was increased relative to the amount of CA.

TABLE 15.3

| Example | CA/PEG Ratio (by weight) | Water Flux (40/75) (g/hr · cm$^2$) |
|---|---|---|
| 15A | 7:3 | $1.7 \times 10^{-3}$ |
| 15B | 8:2 | $1.4 \times 10^{-3}$ |
| 15C | 9:1 | $1.1 \times 10^{-3}$ |

Examples 16A-16U

These examples measure the "durability" of the coating, a relative measure of the strength of the coatings found to be a useful measure for comparing coatings. For Examples 16A-16G, tablets were made as in Example 1, with the exceptions noted in Tables A and B. As indicated in Table C, two different types of coatings and various coating weights were used to coat these tablets. The tablets were made using ¹³⁄₃₂-inch tooling, yielding tablets with a maximum cross-sectional area of 0.84 cm². For Examples 16H-16U, tablets were made as in Example 14, with the exceptions noted in Tables A and B. These tablets were coated with various coating weights, as indicated in Table C. The tablets were made using ⁷⁄₁₆-inch tooling, yielding tablets with a maximum cross-sectional area of 0.97 cm². Table 16.1 lists the compositions and coating weights for the tablets of Example 16. Acetone was used as the solvent in all cases.

To determine the coating durability, the tablets were placed in deionized water at 37° C. for 16 to 24 hours. The tablets were then removed, rinsed in deionized water, and tested for hardness on a Schleuniger tablet hardness tester, Model 6D. Tablets were placed in the tester so that the delivery port was blocked against the tester plate when force was applied. The durability for each tablet, defined as the tablet hardness (in Kp) divided by the maximum cross-sectional surface area (in cm²), was calculated from these tests, and is set forth in Table 16.2.

TABLE 16.1

| | Coating-Solution Formulation (wt %) | | | Coating Weight per Tablet |
|---|---|---|---|---|
| Example | CA 398-10 | PEG | Water | Wt % |
| 16A | 4 | 1 | 2.5 | 11.7 |
| 16B | 4 | 1 | 2.5 | 11.2 |
| 16C | 8 | 2 | 5 | 6.9 |
| 16D | 7 | 3 | 5 | 8.1 |
| 16E | 7 | 3 | 5 | 8.3 |
| 16F | 7 | 3 | 5 | 12.0 |
| 16G | 7 | 3 | 5 | 12.8 |
| 16H | 7 | 3 | 5 | 12.4 |
| 16I | 7 | 3 | 5 | 11.1 |
| 16J | 7 | 3 | 5 | 10.3 |
| 16K | 7 | 3 | 5 | 7.9 |
| 16L | 7 | 3 | 5 | 11.7 |
| 16M | 7 | 3 | 5 | 22.8 |
| 16N | 7 | 3 | 5 | 13.4 |
| 16O | 7 | 3 | 5 | 18.0 |
| 16P | 7 | 3 | 5 | 21.6 |
| 16Q | 7 | 3 | 5 | 26.8 |
| 16R | 7 | 3 | 5 | 13.6 |
| 16S | 7 | 3 | 5 | 18.2 |
| 16T | 7 | 3 | 5 | 21.4 |
| 16U | 7 | 3 | 5 | 25.2 |

TABLE 16.2

| Example | Durability (Kp/cm$^2$) |
|---|---|
| 16A | 30.3 |
| 16B | 20.5 |
| 16C | 4.3 |
| 16D | 10.3 |
| 16E | 7.6 |
| 16F | 13.4 |
| 16G | 12.7 |
| 16H | 8.5 |
| 16I | 7.7 |
| 16J | 7.6 |
| 16K | 4.0 |
| 16L | 6.0 |
| 16M | 22.6 |
| 16N | 13.8 |
| 16O | 18.7 |
| 16P | 22.8 |
| 16Q | 30.6 |
| 16R | 13.7 |
| 16S | 17.3 |
| 16T | 23.0 |
| 16U | 29.8 |

These data show that the durabilities of the high permeability coatings of the present invention are high, and that the coating durability increases as the amount of coating applied to the tablet increases. The data also show that for the same amount of coating, coatings made with a high CA/PEG ratio (Examples 16A to 16C) have a higher durability than those made with a low CA/PEG ratio (Examples 16D to 16U). These results, combined with the results of Example 15, show that the coatings of the present invention have high water permeability and high strength.

Examples 17A-17C

Including solubilizing acids in the drug-containing composition may increase the bioavailability of the drug. These examples demonstrate the utility of the present invention to release an organic acid with Drug 2, sertraline. Here, it is desirable that the solubilizing acid is released along with the sertraline, so as to increase the solubility of sertraline in the use environment, which in turn increases bioavailability.

In Examples 17A-17C, dosage forms of the present invention were made wherein the drug-containing composition or the water-swellable composition included a solubilizing acid selected from citric acid and fumaric acid. These tablets were made as in Example 3A, with the exceptions noted in Tables A, B, and C. In Example 17A, the drug-containing composition contained 15 wt % citric acid. In Example 17B, the drug-containing composition contained 7 wt % fumaric acid. In Example 17C, both the drug-containing composition and the water-swellable composition contained 15 wt % citric acid.

The tablets were dissolution-tested in USP sodium acetate buffer, using the direct test. The results for Examples 17A-C are shown in Tables 17.1 and 17.2 and are summarized in Table D.

TABLE 17.1

| Example | Time (hours) | Drug (wt % released) |
|---|---|---|
| 17A | 0 | 0 |
|  | 1 | 0 |
|  | 2 | 3 |
|  | 4 | 23 |
|  | 6 | 47 |
|  | 8 | 69 |
|  | 10 | 88 |
|  | 12 | 91 |
|  | 16 | 82 |
|  | 20 | 92 |
|  | 24 | 92 |
| 17B | 0 | 0 |
|  | 1 | 0 |
|  | 2 | 9 |
|  | 4 | 31 |
|  | 6 | 57 |
|  | 8 | 79 |
|  | 10 | 92 |
|  | 12 | 96 |
|  | 16 | 96 |
|  | 20 | 96 |

TABLE 17.2

| Example | Time (hours) | Drug (wt % released) | Citric Acid (wt % released) |
|---|---|---|---|
| 17C | 0 | 0 | 0 |
|  | 1 | 0 | 0 |
|  | 2 | 6 | 9 |
|  | 4 | 24 | 28 |
|  | 6 | 46 | 47 |
|  | 8 | 65 | 62 |
|  | 10 | 81 | 76 |
|  | 12 | 94 | 84 |
|  | 16 | 96 | 89 |
|  | 20 | 96 | 93 |

The results of Examples 17A and 17B show that high rates of sertraline release (91% and 96% within 12 hours, respectively) may be obtained when including the solubilizing acid in the dosage form. Comparison with dosage forms that do not contain the solubilizing acid (e.g., Example 14) shows that solubilizing acids did not affect the release profile for the drug.

The results of Example 17C show that the citric acid was released at about the same rate as the sertraline (84% citric acid and 94% sertraline within 12 hours). In addition, citric acid was released at all times when sertraline was released. During the release tests of Examples 17A-C, the receptor solution in the vicinity of the tablets had a pH of about 3, indicating that including organic acids in the dosage form leads to a locally low pH. This test demonstrates that one may expect that the use environment will contain sufficient solubilizing acid in the vicinity of where the drug is released to result in a locally lower pH, in turn causing higher concentration of dissolved drug and, hence, increased bioavailability.

Example 18

This example demonstrates the in vivo release of carprofen (Drug 6) from bi-layer tablets. The solubility of Drug 6 is approximately 0.015 mg/mL at pH 5.9. For the tablets of Example 18, the drug-containing composition was composed of 12.6 wt % Drug 6, 52.4 wt % XYLITAB 200, 28.8 wt % PEO with an average molecular weight of 600,000, 5.0 wt % Explotab, and 1.2 wt % magnesium stearate; and the water-swellable composition was composed of 74.4 wt % EXPLOTAB, 24.6 wt % microcrystalline cellulose (AVICEL pH 200), and 1.0 wt % magnesium stearate. These tablets were made by a direct blend-and-compress method using a single-station Manesty f-press with $^{13}/_{32}$ inch standard round concave tooling. For these tablets, the drug-containing composition made up 400 mg while the water-swellable composition made up 100 mg. Tablets contained 50 mg of active drug. The bi-layer core was then coated with a coating solution consisting of 7 wt % cellulose acetate, 3 wt % PEG 3350, 5 wt % water, and 85 wt % acetone to obtain a coating weight of 11 wt % (wt/wt core), and four 1 mM slits were made on the tablet edge. In vivo residual tests were performed in 5 dogs as follows: one tablet was orally administered to each dog followed by a 50 mL gavage. The bowel movements were screened for tablets and the recovery times noted. The residual undelivered drug was determined by a residual test, and the drug release was calculated by subtracting the residual amount from the known initial amount of drug present in the tablets. Results are shown in Table 18.1.

TABLE 18.1

| Time (hours) | Drug (wt % released) |
|---|---|
| 9 | 48, 57, 58 |
| 20 | 84, 92 |

These tablets were also tested in vitro using a residual dissolution test. These tests were performed in a USP type 2 dissoette using the following conditions: 37° C., 100 rpm, 0.05 M phosphate buffer at pH 7.5. Results are shown in Table 18.2.

TABLE 18.2

| Time (hours) | Drug (wt % released) |
|---|---|
| 0 | 0 |
| 2 | 12 |
| 4 | 37 |
| 8 | 66 |
| 12 | 78 |
| 20 | 95 |
| 24 | 98 |

The data show satisfactory in vivo drug delivery with dosage forms of the invention. Good correlation is observed between in vitro and in vivo data.

Example 19

This example demonstrates the in vivo delivery of Tenidap (Drug 7) from bi-layer tablets. The solubility of Drug 7 is 0.2 mg/mL at pH 7.4 and 0.002 mg/mL at pH 3.7. For the tablets of Example 19, the drug-containing composition consisted of 12.5% Drug 7, 37.5 wt % XYLITAB 200, 36.15 wt % PEO with an average molecular weight of 600,000, 12.5 wt % EXPLOTAB, and 1.25 wt % magnesium stearate; and the water-swellable composition consisted of 74.0 wt % EXPLOTAB, 24.5 wt % microcrystalline cellulose (AVICEL pH 200), 0.5 wt % FD&C Red, and 1.0 wt % magnesium stearate. These tablets were made using a direct blend-and-compress manufacturing process on a single-station Manesty f-press. For these tablets, the drug-containing composition made up 400 mg and the water-swellable composition made up 100 mg. Tablets contained 50 mg active Drug 7. The bi-layer core was then coated in a Freund HCT-30 EP coating pan using a spray solution consisting of 7 wt % cellulose acetate, 3 wt % PEG, 5 wt % water, and 85 wt % acetone to obtain a coating weight of 10% (wt/wt core). Instead of drilling a delivery port, four slits in the coating were made on the edge of each tablet.

In vivo residual tests were performed in dogs as follows: Each of five dogs were dosed with tablets (so that they could be later identified) over a six-hour period (i.e., one tablet every two hours) with oral gavage of 50 mL water. The bowel movement was screened for tablets and the recovery time noted. All tablets were recovered intact, i.e., there were no splits in the coatings. The amount of undelivered drug was determined by extracting the unreleased drug from the tablets and the drug released was determined by subtracting the unreleased amount from the known initial amount of drug present in the tablets. Results are shown in Table 19.1.

TABLE 19.1

| Time (hours) | Drug (wt % released) |
| --- | --- |
| 4 | 25.8 (n = 2) |
| 6 | 43.9 (n = 2) |
| 8 | 59.7 (n = 1) |
| 20 | 74.9 (n = 3) |
| 21.5 | 83.3 (n = 1) |
| 22.0 | 80.2 (n = 2) |
| 23.5 | 87.7 (n = 1) |
| 24.0 | 83.6 (n = 2) |
| 25.5 | 87.0 (n = 1) |

In addition to the in vivo test above, residual recovery from a pharmacokinetic (PK) study in dogs was performed as follows: dogs were dosed with one tablet each and blood samples withdrawn periodically at selected times. The bowel movements were screened for tablets and the recovery times noted. The residual undelivered drug was determined by extraction and the drug released calculated as described previously. The results from the residual PK study agree with the results above; they are shown in Table 19.2.

TABLE 19.2

| Time (hours) | Drug (wt % released) |
| --- | --- |
| 8 | 57.8 (n = 2) |
| 16-25 | 83.4 (n = 2) |

These tablets were also tested in vitro using a residual dissolution. The dissolution of tablets with one slit on the tablet face is shown for comparison. These tests were performed using a USP type 2 dissoette under the following conditions: 900 mL pH 7.5 phosphate buffer, 100 rpm, 37° C. Results are shown in Table 19.3.

TABLE 19.3

| Time (hours) | Drug (wt % released) 4 slits on edge | Drug (wt % released) 1 slit on face |
| --- | --- | --- |
| 0 | 0 | 0 |
| 2 | 16 | 6 |
| 4 | 43 | 24 |
| 8 | 75 | 61 |
| 12 | 84 | 80 |
| 20 | 91 | 94 |
| 24 | 94 | 94 |

The data show satisfactory in vivo drug delivery with dosage forms of the invention. Good correlation is observed between in vitro and in vivo data.

Example 20

This example shows the utility of including a concentration-enhancing polymer, a solubilizer, and a fluidizing agent in the drug-containing composition. The drug-containing composition comprised the following materials: 20 wt % Drug 2, 15 wt % tartaric acid (a solubilizer), 20 wt % HPMCAS (HPMCAS-LG grade) (a concentration-enhancing polymer), 29 wt % PEO with an average molecular weight of 600,000 (Polyox WSR-205) (a polymeric entraining agent), 15 wt % xylitol (Xylitab 200) (a fluidizing agent), and 1 wt % of the lubricant, magnesium stearate. To form the drug-containing composition, the ingredients (without the magnesium stearate) were blended for 10 minutes in a Turbula mixer. This blend was wet-granulated using a mortar and pestle with a mixture of isopropyl alcohol and water in a volume ratio of 85:15. The wet-granulated material was dried in a 40° C. oven overnight. The dried granulation was passed through a Fitzpatrick hammer mill, model L1A, at 3000 rpm, and screened through a 0.065-inch screen. This material was blended again in the Turbula mixer for 10 minutes. Next, magnesium stearate was added and the materials were blended for 4 additional minutes.

The water-swellable composition comprised the following materials: 64.4 wt % PEO with an average molecular weight of 5 million (Polyox WSR Coagulant), 30 wt % sodium chloride, 5 wt % HPMC (Methocel E5 LV Prem., a tablet binder), 0.1 wt % of a colorant (Red Lake #40), and 0.5 wt % magnesium stearate. To form the water-swellable composition, the ingredients (without the colorant or magnesium stearate) were blended 20 minutes in a twinshell mixer, then milled using a hammer mill and passed through a 0.098-inch screen. This material was blended again for 20 minutes in a twinshell mixer. The colorant and magnesium stearate were mixed for 1 minute, and then added to the blend. These ingredients were blended for 4 additional minutes.

The drug-containing composition and the water-swellable composition were tableted together using direct compression to form the core. A portion of the drug-containing composition (441.5 mg) was placed in an f-press with a standard round concave 7/16-inch die, then gently leveled with the upper punch. A portion of the water-swellable composition (227.5 mg) was placed on top of the layer of drug-containing composition and compressed. The compression distance between the upper and lower punches on the f-press was adjusted until the hardness of the resulting core measured 11.4 Kp. The resulting bi-layer core weighed 669 mg and contained a total of 13.2 wt % sertraline HCl, 9.9 wt % tartaric acid, 13.2 wt % HPMCAS-LG, 19.1 wt % PEO 600,000, 9.9 wt % xylitol, 0.9 wt % magnesium stearate, 21.9 wt % PEO 5,000,000, 10.2 wt % sodium chloride, 1.7 wt % HPMC, and 0.03 wt % colorant. Assays of these tablets showed 82 mg of Sertraline HCl, or 73 mgA of active sertraline.

The tablets were coated with a high water permeability coating in a Vector LDCS-20 pan coater. The coating solution contained CA 398-10, polyethylene glycol (PEG 3350), water, and acetone in a weight ratio of 7/3/5/85. Heated drying air (40 cfm) was adjusted to maintain the pan coater outlet temperature at 25° C. Nitrogen at 20 psi was used to atomize the coating solution from the spray nozzle, with a nozzle-to-bed distance of 2 inches. The pan tumbled at 20 rpm. The final dry coating weight amounted to 20.4 wt % of the weight of the tablet core. One 2 mM port was laser-drilled on the face of the tablet. The total weight of the coated tablet was 805 mg.

An in vitro residual drug release test was performed. Tablets were placed in a stirred USP type 2 dissoette flask containing a solution of gastric buffer (10 mM HCl, 100 mM NaCl, pH 2.0, 261 mOsm/kg) for 2 hours, and then transferred to a solution of intestinal buffer (6 mM $KH_2PO_4$, 64 mM KCl, 35 mM NaCl, pH 7.2, 210 mOsm/kg). In both flasks, the dosage form was placed in a wire support to keep the tablet off of the bottom of the flask so that all surfaces were exposed to the solution, and the solutions were stirred using paddles rotating at 50 revolutions per minute. At spaced-apart time intervals, a single tablet was removed and placed in recovery solution (50/50 wt/wt ethanol/water, pH 3) to dissolve the drug remaining in the tablet. Residual drug was analyzed by HPLC using a Phenomenex Ultracarb 5 ODS 20 column. The mobile phase consisted of 35 vol % TEA-acetate buffer (3.48 mL triethanolamine and 2.86 mL glacial acetic acid in 1 L HPLC-grade $H_2O$) in acetonitrile. Drug concentration was calculated by comparing UV absorbance at 230 nm to the absorbance of known drug standards. The amount remaining in the tablets was subtracted from the initial amount of drug in the tablets (73 mgA) to obtain the amount released at each time interval. Results are shown in Table 20 and are summarized in Table D.

TABLE 20

| Time (hours) | Drug (wt % A released) |
| --- | --- |
| 0 | 0 |
| 1 | 3 |
| 2 | 4 |
| 4 | 32 |
| 8 | 74 |
| 12 | 78 |
| 16 | 86 |
| 20 | 89 |

The data show that 4 wt % A of the drug was released within 2 hours, and that 74 wt % A of the drug was released within 8 hours. After 20 hours, 89% of the drug contained in the tablet had been released. Observations of the tablets during the release test indicated that the coating remained intact for the duration of the test.

For comparison, identical tablets were prepared but without the fluidizing agent xylitol. During dissolution tests of these tablets, it was observed that the coating on one out of every 4 tablets split. Thus, including a fluidizing agent in the formulation (as in Example 20) reduced the pressure at which the drug-containing composition was delivered through the delivery ports.

TABLE A

Summary of Drug-Containing Composition for All Examples

| Example | Drug | [Drug] wt % | [PEO] Type | [PEO] wt % | [Explotab] wt % | [Xylitab 200] wt % | [Mg Stearate] wt % | Other Ingredients | Conc. wt % | Processing Method |
| --- | --- | --- | --- | --- | --- | --- | --- | --- | --- | --- |
| 1 | 1 | 35 | 600K | 29 | 5.0 | 30.0 | 1.0 | | | Dry Blended |
| 2 | 1 | 56 | 600K | 19 | 4.0 | 20.0 | 1.0 | | | Dry Blended |
| 3A | 2 | 35.0 | 600K | 28.75 | 5.0 | 30.0 | 1.25 | | | Dry Blended |
| 3B | 3 | 32.4 | 600K | 29.9 | 5.2 | 31.2 | 1.3 | | | Dry Blended |
| 4 | 2 | 35.0 | 600K | 29.0 | 5.0 | 30.0 | 1.0 | | | Dry Blended |
| 5A | 1 | 35.0 | 600K | 29 | 5 | 30 | 1.0 | | | Wet granulated |
| 5B | 1 | 35.0 | 600K | 29 | 5 | 30 | 1.0 | | | Wet granulated |
| 5C | 1 | 35.0 | 600K | 29 | 5 | 30 | 1.0 | | | Wet granulated |
| 6 | 1 | 56.0 | 600K | 19.0 | 4.0 | 20.0 | 1.0 | | | Dry Blended |
| 7A | 1 | 35 | 600K | 29.0 | 5.0 | 30.0 | 1.0 | | | Dry Blended |
| 7B | 1 | 35 | 600K | 29.0 | 5.0 | 30.0 | 1.0 | | | Dry Blended |
| 7C | 1 | 35 | 600K | 29.0 | 5.0 | 30.0 | 1.0 | | | Dry Blended |
| 7D | 1 | 35 | 600K | 29.0 | 5.0 | 30.0 | 1.0 | | | Dry Blended |
| 8 | 2 | 20.57 | 600K | 26.75 | 4.33 | 26.75 | 1.0 | HPMCP | 20.57 | Precompressed, comilled |
| 9 | 4 | 22.2 | 600K | 25.2 | 3.5 | 26.1 | 0.8 | HPMCAS-MF | 22.2 | Dry Blended |
| 10 | 5 | 4.16 | 600K | 25 | 3.9 | 25 | 1.0 | HPMCAS-HF | 40.94 | Dry Blended |
| 11 | 2 | 22.8 | 200K | 71.7 | 0 | 0 | 0.5 | Methocel K3LV | 5.0 | Dry Blended |
| 13 | 2 | 22.8 | 200K | 71.7 | 0 | 0 | 0.5 | Methocel K3LV | 5.0 | Dry Blended |
| 14 | 2 | 35 | 200K | 59.6 | 0 | 0 | 0.5 | Methocel K3LV | 5.0 | Dry Blended |
| 15A | 2 | 22.8 | 200K | 71.7 | 0 | 0 | 0.5 | Methocel K3LV | 5.0 | Dry Blended |
| 15B | 2 | 22.8 | 200K | 71.7 | 0 | 0 | 0.5 | Methocel K3LV | 5.0 | Dry Blended |

TABLE A-continued

Summary of Drug-Containing Composition for All Examples

| Example | Drug | [Drug] wt % | [PEO] Type | [PEO] wt % | [Explotab] wt % | [Xylitab 200] wt % | [Mg Stearate] wt % | Other Ingredients | Conc. wt % | Processing Method |
|---|---|---|---|---|---|---|---|---|---|---|
| 15C | 2 | 22.8 | 200K | 71.7 | 0 | 0 | 0.5 | Methocel K3LV | 5.0 | Dry Blended |
| 16A-16G | 1 | 35 | 600K | 29 | 5.0 | 30.0 | 1.0 | | | Dry Blended |
| 16H-16U | 2 | 35 | 200K | 59.6 | 0 | 0 | 0.5 | Methocel K3LV | 5.0 | Dry Blended |
| 17A | 2 | 30 | 200K | 49.5 | 0 | 0 | 1.5 | Klucel EF Citric acid | 4.5 15.0 | Dry Blended |
| 17B | 2 | 37.8 | 200K | 48.8 | 0 | 0 | 1.0 | Klucel EF Fumaric acid | 4.9 7.0 | Dry Blended |
| 17C | 2 | 29.9 | 200K | 49.2 | 0 | 0 | 1.5 | Klucel EF Citric acid | 4.5 14.9 | Dry Blended |
| 18 | 6 | 12.6 | 600K | 28.8 | 5.0 | 52.4 | 1.2 | | | Dry Blended |
| 19 | 7 | 12.5 | 600K | 36.15 | 12.5 | 37.5 | 1.25 | | | Dry Blended |
| 20 | 2 | 20 | 600K | 29 | 0 | 15 | 1.0 | Tartaric acid HPMCAS | 15 20 | Blended, wet-granulated w/IPA/H2O (85/15), dried, milled, blended |

TABLE B

Summary of Water-Swellable Composition for All Examples

| Example | [Explotab] wt % | [Prosolv 90] wt % | [Mg Stearate] wt % | Other Ingredients | Conc. wt % | Processing Method |
|---|---|---|---|---|---|---|
| 1 | 74.5 | 25 | 0.5 | | | Dry Blended |
| 2 | 74.5 | 25 | 0.5 | | | Dry Blended |
| 3A | 74.5 | 25 | 0.5 | | | Dry Blended |
| 3B | 74.5 | 24.5 | 1.0 | | | Dry Blended |
| 4 | 0 | 0 | 0.6 | Methocel K3LV PEO 5 million NaCl | 5.0 65.0 29.4 | Dry Blended |
| 5A | 74.35 | 24.85 | 0.3 | Red Lake#40 | 0.3 | Wet granulated |
| 5B | 49.4 | 49.4 | 1.0 | Red Lake#40 | 0.25 | Wet granulated |
| 5C | 59.35 | 39.4 | 1.0 | Red Lake#40 | 0.25 | Wet granulated |
| 6 | 74.3 | 25.2 | 0.5 | | | Dry Blended |
| 7A | 74.35 | 24.85 | 0.3 | Red Lake#40 | 0.3 | Dry Blended |
| 7B | 74.35 | 24.85 | 0.3 | Red Lake#40 | 0.3 | Dry Blended |
| 7C | 74.35 | 24.85 | 0.3 | Red Lake#40 | 0.3 | Dry Blended |
| 7D | 74.35 | 24.85 | 0.3 | Red Lake#40 | 0.3 | Dry Blended |
| 8 | 74.66 | 24.73 | 0.47 | Red Lake#40 | 0.14 | Dry Blended |
| 9 | 74.8 | 24.8 | 0.4 | | | Dry Blended |
| 10 | 74.8 | 24.7 | 0.5 | | | Dry Blended |
| 11 | 74.5 | 25.0 | 0.5 | | | Dry Blended |
| 13 | 0 | 0 | 0.6 | Methocel K3LV PEO 5 million NaCl | 5.1 65.0 29.3 | Dry Blended |
| 14 | 0 | 0 | 0.6 | Methocel K3LV PEO 5 million NaCl | 5.1 65.0 29.3 | Dry Blended |
| 15A | 0 | 0 | 0.6 | Methocel K3LV PEO 5 million NaCl | 5.1 65.0 29.3 | Dry Blended |
| 15B | 0 | 0 | 0.6 | Methocel K3LV PEO 5 million NaCl | 5.1 65.0 29.3 | Dry Blended |
| 15C | 0 | 0 | 0.6 | Methocel K3LV PEO 5 million NaCl | 5.1 65.0 29.3 | Dry Blended |
| 16A-16G | 74.5 | 25 | 0.5 | | | Dry Blended |
| 16H-16U | 0 | 0 | 0.6 | Methocel K3LV PEO 5 million NaCl | 5.1 65.0 29.3 | Dry Blended |
| 17A | 0 | 0 | 0.6 | Methocel K3LV PEO 5 million NaCl | 5.9 64.3 29.2 | Dry Blended |
| 17B | 0 | 0 | 0.5 | Methocel K3LV PEO 5 million NaCl Red Lake #40 | 5.1 64.4 29.9 0.1 | Dry Blended |
| 17C | 0 | 0 | 0.6 | Methocel K3LV PEO 5 million NaCl Citric acid | 5.9 64.3 14.6 14.6 | Dry Blended |

TABLE B-continued

Summary of Water-Swellable Composition for All Examples

| Example | [Explotab] wt % | [Prosolv 90] wt % | [Mg Stearate] wt % | Other Ingredients | Conc. wt % | Processing Method |
|---|---|---|---|---|---|---|
| 18 | 74.4 | 0 | 1.0 | Avicel | 24.6 | Dry Blended |
| 19 | 74.0 | 0 | 1.0 | Avicel | 24.5 | Dry Blended |
|  |  |  |  | Red Lake #40 | 0.5 |  |
| 20 | 0 | 0 | 0.5 | Methocel K3LV | 5.0 | Dry Blended |
|  |  |  |  | PEO 5 million | 64.4 |  |
|  |  |  |  | NaCl | 30.0 |  |
|  |  |  |  | Red Lake #40 | 0.1 |  |

TABLE C

Summary of Details of Tablet Formulations for All Examples

| Example | Core Weight (mg) | Drug Layer | Sweller Layer | Ratio of Drug to Sweller layer (w/w) | [CA] wt % | [PEG] wt % | [H2O] wt % | Coating Amount wt % of uncoated tablet | Number of Ports | Port size (μm) |
|---|---|---|---|---|---|---|---|---|---|---|
| 1 | 500 | 400 | 100 | 4.0 | 7 | 3 | 5 | 8.1 | 5 | 900 |
| 2 | 600 | 500 | 100 | 5.0 | 7 | 3 | 5 | 10.6 | 5 | 900 |
| 3A | 500 | 400 | 100 | 4.0 | 7 | 3 | 5 | 9.6 | 5 | 900 |
| 3B | 500 | 400 | 100 | 4.0 | 7 | 3 | 5 | 10.2 | 5 | 900 |
| 4 | 735 | 490 | 245 | 2.0 | 7 | 3 | 5 | 13.0 | 1 | 900 |
| 5A | 500 | 400 | 100 | 4.0 | 7 | 3 | 5 | 8.1 | 5 | 900 |
| 5B | 500 | 400 | 100 | 4.0 | 7 | 3 | 5 | 9.3 | 5 | 900 |
| 5C | 500 | 400 | 100 | 4.0 | 7 | 3 | 5 | 8.7 | 5 | 900 |
| 6 | 700 | 500 | 200 | 2.5 | 7 | 3 | 5 | 11.1 | 5 | 900 |
| 7A | 500 | 400 | 100 | 4.0 | 7 | 3 | 5 | 5.8 | 5 | 900 |
| 7B | 500 | 400 | 100 | 4.0 | 7 | 3 | 5 | 11.3 | 5 | 900 |
| 7C | 500 | 400 | 100 | 4.0 | 7 | 3 | 5 | 17.9 | 5 | 900 |
| 7D | 500 | 400 | 100 | 4.0 | 7 | 3 | 5 | 24.9 | 5 | 900 |
| 8 | 700 | 550 | 150 | 3.7 | 7 | 3 | 5 | 9.7 | 5 | 2000 |
| 9 | 600 | 450 | 150 | 3.0 | 7 | 3 | 5 | 8.9 | 5 | 900 |
| 10 | 700 | 550 | 150 | 3.7 | 7 | 3 | 5 | 11.3 | 5 | 900 |
| 11 | 735 | 490 | 245 | 2.0 | 7 | 3 | 5 | 12.6 | 1 | 900 |
| 13 | 735 | 490 | 245 | 2.0 | 7 | 3 | 5 | 12.9 | 1 | 900 |
| 14 | 735 | 490 | 245 | 2.0 | 7 | 3 | 5 | 13.0 | 1 | 900 |
| 15A | 735 | 490 | 245 | 2.0 | 7 | 3 | 5 | 11.2 | 1 | 900 |
| 15B | 735 | 490 | 245 | 2.0 | 8 | 2 | 5 | 11.4 | 1 | 900 |
| 15C | 735 | 490 | 245 | 2.0 | 9 | 1 | 5 | 11.7 | 1 | 900 |
| 16A | 500 | 400 | 100 | 4.0 | 4 | 1 | 2.5 | 11.7 | 5 | 900 |
| 16B | 500 | 400 | 100 | 4.0 | 4 | 1 | 2.5 | 11.2 | 5 | 900 |
| 16C | 500 | 400 | 100 | 4.0 | 8 | 2 | 5 | 6.9 | 5 | 900 |
| 16D | 500 | 400 | 100 | 4.0 | 7 | 3 | 5 | 8.1 | 5 | 900 |
| 16E | 500 | 400 | 100 | 4.0 | 7 | 3 | 5 | 8.3 | 5 | 900 |
| 16F | 500 | 400 | 100 | 4.0 | 7 | 3 | 5 | 12.0 | 5 | 900 |
| 16G | 500 | 400 | 100 | 4.0 | 7 | 3 | 5 | 12.8 | 5 | 900 |
| 16H | 735 | 490 | 245 | 2.0 | 7 | 3 | 5 | 12.4 | 1 | 900 |
| 16I | 735 | 490 | 245 | 2.0 | 7 | 3 | 5 | 11.1 | 1 | 900 |
| 16J | 735 | 490 | 245 | 2.0 | 7 | 3 | 5 | 10.3 | 1 | 900 |
| 16K | 735 | 490 | 245 | 2.0 | 7 | 3 | 5 | 7.9 | 1 | 900 |
| 16L | 735 | 490 | 245 | 2.0 | 7 | 3 | 5 | 11.7 | 1 | 900 |
| 16M | 735 | 490 | 245 | 2.0 | 7 | 3 | 5 | 22.8 | 1 | 900 |
| 16N | 735 | 490 | 245 | 2.0 | 7 | 3 | 5 | 13.4 | 1 | 900 |
| 16O | 735 | 490 | 245 | 2.0 | 7 | 3 | 5 | 18.0 | 1 | 900 |
| 16P | 735 | 490 | 245 | 2.0 | 7 | 3 | 5 | 21.6 | 1 | 900 |
| 16Q | 735 | 490 | 245 | 2.0 | 7 | 3 | 5 | 26.8 | 1 | 900 |
| 16R | 735 | 490 | 245 | 2.0 | 7 | 3 | 5 | 13.6 | 1 | 900 |
| 16S | 735 | 490 | 245 | 2.0 | 7 | 3 | 5 | 18.2 | 1 | 900 |
| 16T | 735 | 490 | 245 | 2.0 | 7 | 3 | 5 | 21.4 | 1 | 900 |
| 16U | 735 | 490 | 245 | 2.0 | 7 | 3 | 5 | 25.2 | 1 | 900 |
| 17A | 887 | 591 | 296 | 2.0 | 7 | 3 | 5 | 21.9 | 1 | 700 |
| 17B | 700 | 469 | 231 | 2.0 | 7 | 3 | 5 | 20.0 | 1 | 700 |
| 17C | 887 | 591 | 296 | 2.0 | 7 | 3 | 5 | 21.9 | 1 | 700 |
| 18 | 500 | 400 | 100 | 4.0 | 7 | 3 | 5 | 11 | 4 | 1000 (slits) |
| 19 | 500 | 400 | 100 | 4.0 | 7 | 3 | 5 | 10 | 4 | 1000 (slits) |
| 20 | 669 | 441.5 | 227.5 | 1.9 | 7 | 3 | 5 | 20.4 | 1 | 2000 |

TABLE D

Summary of Release Rates in wt % for All Examples*

| Example | 2-hr release (%) | 8-hr release (%) | 12-hr release (%) | 16-hr release (%) | 20-hr release | 24-hr release (%) |
|---|---|---|---|---|---|---|
| 1 | 25 | 74 | 87 | 95 | 98 | |
| 2 | 16 | 57 | 70 | 78 | 86 | |
| 3A | 22 | 79 | 88 | 93 | 94 | |
| 3B | 18 | 68 | 85 | 88 | | 91 |
| 4 | 15 | 80 | 90 | 93 | | 87 |
| 5A | 15 | 69 | 86 | 95 | 97 | |
| 5B | 15 | 67 | 82 | 91 | 96 | |
| 5C | 16 | 69 | 82 | 91 | 96 | |
| 6 | 16 | 65 | 81 | 91 | 94 | |
| 7A | 30 | 88 | 95 | 98 (14-hr) | 97 | |
| 7B | 19 | 69 | 86 | 95 | 98 | |
| 7C | 8 | 60 | 75 | 85 | 94 | |
| 7D | 0 | 48 | 61 | 75 | 88 | |
| 8 | 17 | 68 | 86 | 89 | | 86 |
| 9 | 4 | 63 | 81 | 91 | | 97 |
| 10 | 13 | 46 | 73 | 75 | | 74 |
| 11 | 17 | 70 | 84 | 86 | | 92 |
| 13 | 19 | 98 | 99 | 99 | | 99 |
| 14 | 25 | 97 | 98 | 98 | | 98 |
| 17A | 3 | 69 | 91 | 82 | | 92 |
| 17B | 9 | 79 | 96 | 96 | 96 | |
| 17C (drug) | 6 | 65 | 94 | 96 | 96 | |
| 17C (citric acid) | 9 | 62 | 84 | 89 | 93 | |
| 18 | 12 | 66 | 78 | 87 | | 98 |
| 19 (in vivo) | 12.9 | 59.7 | 64.8 | 69.8 | | 83.6 |
| 20 | 4 | 74 | 78 | 86 | 89 | |

*some values are interpolated from concentrations obtained at other time points

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A controlled release drug dosage form comprising a core and a coating around said core, said coating consisting of a mixture of cellulose acetate and polyethylene glycol, wherein said core comprises a drug-containing composition and a water-swellable composition, each occupying separate regions within said core and wherein
  (a) said drug-containing composition comprises a drug, the drug-entraining agent polyethylene oxide, and the fluidizing agent selected from the group consisting of sugars and organic acids; and
  (b) said coating is water-permeable, water-insoluble, has at least one delivery port therethrough, and a durability of at least 1 Kp/cm²; and wherein said coating is formed from a substantially homogeneous solution comprising a solvent, said cellulose acetate, said polyethylene glycol, and at least 4 wt % of the non-solvent water but not greater than a weight percent such that a cloud point of the solution is reached when the solution is at room temperature, wherein a weight ratio of cellulose acetate to polyethylene glycol of from 8:2 to 6.5:3.5.

2. The dosage form of claim 1 wherein said coating is formed from a solution containing at least 15 wt % water but not greater than a weight percent such that a cloud point of the solution is reached.

3. The dosage form of claim 1, wherein said water swellable composition comprises polyethylene oxide, microcrystalline cellulose, and an osmagent selected from magnesium sulfate, magnesium chloride, calcium chloride, sodium chloride, lithium chloride, potassium sulfate, sodium carbonate, sodium sulfite, lithium sulfate, potassium chloride, sodium sulfate, d-mannitol, urea, sorbitol, inositol, raffinose, sucrose, glucose, fructose, lactose, and mixtures thereof.

* * * * *